(12) United States Patent
Fermier et al.

(10) Patent No.: US 7,045,288 B2
(45) Date of Patent: May 16, 2006

(54) APPARATUS FOR THE AUTOMATION OF CHEMICAL REACTION KINETICS STUDIES

(75) Inventors: Adam M. Fermier, Easton, PA (US);
Alan R. Oyler, Flemington, NJ (US);
Barbara L. Armstrong, Somerville, NJ (US); James V. Weber, Newtown, PA (US); James Nalasco, Ewing, NJ (US)

(73) Assignee: Ortho-McNeil Pharmaceutical, Inc, Raritan, NJ (US)

( * ) Notice: Subject to any disclaimer, the term of this patent is extended or adjusted under 35 U.S.C. 154(b) by 596 days.

(21) Appl. No.: 09/816,787

(22) Filed: Mar. 23, 2001

(65) Prior Publication Data

US 2002/0177956 A1 Nov. 28, 2002

(51) Int. Cl.
*C12Q 1/68* (2006.01)
*C07H 19/34* (2006.01)

(52) U.S. Cl. .................. 435/6; 435/91.1; 435/91.2
(58) Field of Classification Search .............. 435/6, 435/91.1, 91.2; 536/21.1; 702/27; 706/47; 712/200

See application file for complete search history.

(56) References Cited

U.S. PATENT DOCUMENTS

| | | | | |
|---|---|---|---|---|
| 5,525,300 A | * | 6/1996 | Danssaert et al. | ............ 422/99 |
| 5,964,095 A | | 10/1999 | Coelho et al. | |
| 2002/0090320 A1 | * | 7/2002 | Burow et al. | ................. 422/64 |

FOREIGN PATENT DOCUMENTS

| FR | 2 633 310 | 12/1989 |
|---|---|---|
| WO | WO97/16717 | 5/1997 |

OTHER PUBLICATIONS

Rogers, A.R., *An Accelerated Storage Test with Programmed Temperature Rise*. J. Pharm. and Pharmacol., 1963. 15: p. 101t-105t.
Davis, R.E., *Temperature as a variable during kinetic experiments*. J. Phys. Chem., 1959. 63: p. 307-309.
Kipp, J.E. and J.J. Hlavaty, *Nonisothermal stability assessment of stable pharmaceuticals: testing of a clindamycin phosphate formulation*. Pharm. Res., 1991. 8(5): p. 570-575.

Junnarkar, G.H. and S. Stavchansky, *Isothermal and nonisothermal decomposition of famotidine in aqueous solution*. Pharm. Res., 1995. 12(4): p. 599-604.
Lee, M.-L. and S. Stavchansky, *Isothermal and nonisothermal decomposition of thymopentin and its analogs in aqueous solution*. Pharm. Res., 1998. 15(11): p. 1702-1707.
Zhan, X., et al., *Exponential Heating in Drug Stability Experiment and Statistical Evaluation of Nonisothermal and Isothermal Prediction*. J. Pharm. Sci., 1997. 86(6): p. 709-715.
Zhan, X., G. Yin, and B. Ma, *Determination of Rate Order for Degradation of Drugs with Nonisothermal Stability Experiment*. J. Pharm. Sci., 1997. 86(10): p. 1099-1104.
Kipp, J.E., et al., *Automated liquid chromatography for non-isothermal kinetic studies*. Int. J. Pharm., 1986. 34(1-2): p. 1-8.
Zhan, X., G. Yin, and B. Ma, *New heating controller and computation for linear heating stability experiment*. Int. J. Pharm., 1995. 115(2): p. 161-166.
Zhan, X., et al., *Computer-controlled heating system and new computation for reciprocal heating stability experiment*. Int. J. Pharm., 1995. 115(2): p. 167-173.

(Continued)

*Primary Examiner*—Kenneth R. Horlick
*Assistant Examiner*—Young J. Kim
(74) *Attorney, Agent, or Firm*—Darby & Darby

(57) ABSTRACT

The present invention relates to an apparatus designed to perform chemical reaction kinetics studies and more particularly to an apparatus which is capable of conducting accelerated automated kinetics studies with user-defined temperature profiles and sampling periods. The apparatus includes at least one hot reaction block for heating one or more reaction vessels and at least one cold reaction block for cooling the one or more reaction vessels after heating thereof. The apparatus includes a robotic device for transferring one reaction vessel from one hot reaction block to one cold reaction block and a controller having a user interface for inputting a predetermined temperature profile and a predetermined sampling interval. The controller is in communication with the plurality of reaction blocks and the robotic device so as to instruct the robotic device to transfer one reaction vessel from one hot reaction block to one cold reaction block at a predefined transfer time within the predetermined sampling interval. The predetermined temperature profile represents the temperature of at least one of the hot reaction blocks over a time period of the study.

34 Claims, 10 Drawing Sheets

OTHER PUBLICATIONS

Tucker, I.G., *An assessment of a logarithmic nonisothermal storage test*. Drug Dev. Ind. Pharm., 1981, 7(2): p. 231-246.

Rosenberg, L.S., et al., *Nonisothermal methods for stability prediction*. J. Parenter. Sci. Technol., 1986. 40(4): p. 164-168.

Cole, B.R. and L. Leadbeater, *A critical assessment of an accelerated storage test*. J. Pharm. Pharmacol., 1966. 18: p. 101-111.

Anderson, R.A. and M. Campbell, *Simple nonisothermal method for predicting stability of pharmaceuticals*. Australas. J. Pharm., 1971. 52(623): p. S81-S83.

Eriksen, S.P. and H. Stelmach, *Single-step stability studies*. J. Pharm. Sci., 1965. 54(7): p. 1029-1034.

Zoglio, M.A., et al., *Linear nonisothermal stability studies [of pharmaceuticals]*. J. Pharm. Sci., 1968. 57(12): p. 2080-2085.

Kay, A.I. and T.H. Simon, *Use of an analog computer to simulate and interpret data obtained from linear nonisothermal stability studies*. J. Pharm. Sci., 1971. 60(2): p. 205-208.

Okusa, N., *Prediction of the stability of drugs. IV. Prediction of the stability by a multilevel nonisothermal method*. Chem. Pharm. Bull., 1975. 23(4): p. 803-809.

Tucker, I.G. and W.R. Owen, *Estimation of all parameters from nonisothermal kinetic data*. J. Pharm. Sci., 1982. 71(9): p. 969-974.

Waltersson, J.O. and P. Lundgren, *Nonisothermal kinetics applied to pharmaceuticals*. Acta Pharm. Suec., 1982. 19(2): p. 127-136.

Ahlneck, C. and P. Lundgren, *Methods for the evaluation of solid state stability and compatibility between drug and excipient*. Acta Pharm. Suec., 1986. 22(6): p. 305-314.

Edel, B. and M.O. Baltzer, *Nonisothermal kinetics with programmed temperature steps*. J. Pharm. Sci., 1980. 69(3): p. 287-290.

Zoglio, M.A. et al., *Nonisothermal kinetic studies. III. Rapid nonisothermal-isothermal method for stability prediction*. J. Pharm. Sci., 1975. 64(8): p. 1381-1383.

Hodgson, S.C., et al., *A student experiment in non-isothermal chemical kinetics*. J. Chem. Ed., 1998. 75(9): p. 1150-1153.

Maulding, H.V., Jr. and M.A. Zoglio, *Flexible nonisothermal stability studies*. J. Pharm. Sci., 1970. 59(3): p. 333-337.

Yoshioka, S., Y. Aso, and Y. Takeda, *Isothermal and nonisothermal kinetics in the stability prediction of vitamin A preparations*. Pharm. Res., 1990. 7(4): p. 388-391.

Yoshioka, S., Y. Aso, and M. Uchiyama, *Statistical evaluation of nonisothermal prediction of drug stability. II. Experimental design for practical drug products*. Int. J. Pharm., 1988. 46(1-2): p. 121-132.

Tucker, Ian, Nonisothermal stability testing (Pharm. Technol. (1985), 9(5), 68, 70, 72, 74, 76, 78. CODEN: PTECDN ISSN:0147-8087. CAN 103:11286 AN 1985:411286 CAPLUS.

\* cited by examiner

Temperature effects on relative rates and length of degradation studies required.

Data for pH 1.0 reactions: isothermal at 85 °C

Nonisothermal, 50 to 100 °C over 80 hours, linear program

Data for pH 11.7 reactions: isothermal at 85 °C

Nonisothermal, 50 to 100 °C over 160 hours, linear program

"UDUD" temperature program

A=2.43 x $10^{10}$ $h^{-1}$ and E=20.42 Kcal/mole

APPARATUS FOR THE AUTOMATION OF CHEMICAL REACTION KINETICS STUDIES

FIELD OF THE INVENTION

The present invention relates to an apparatus designed to perform chemical reaction kinetics studies and more particularly to an apparatus which is capable of conducting accelerated automated kinetics studies with user-defined temperature profiles and sampling periods.

DESCRIPTION OF THE RELATED ART

As the pharmaceutical drug industry and other related industries become more and more competitive, it has become increasingly more and more important to have an efficient and effective drug development program. Generally, one of the culminating steps of drug development is to submit a new drug application (NDA) to the applicable regulatory authority governing the area. The application process is fairly detailed and time consuming and requires different levels of clinical testing and the like. One of the studies that is involved in the evaluation of a new drug is called a real time stability (RTS) study of the drug product in the final package form for a proposed shelf-life claim (e.g., two years). This is required for filing the NDA. The ability to optimize in an accelerated fashion (e.g., 2 weeks) the outcome of the two year RTS study is essential if one wishes to decrease the time period it takes for completing the NDA and gaining approval of the new drug. Decreasing the overall application time is obviously important for companies competing against one another as each company tries to gain a competitive edge.

Thus, studying drug degradation reaction kinetics is an important part in the timely development of new therapeutic products. These degradation studies include the gathering of data on reaction kinetics as well as product distributions over time. As one of skill in the art understands, over time the sample, e.g., drug, will degrade and form various products. Part of the overall study is to determine what products have been formed and the relative distribution of these products relative to one another. The data can be used to optimize the RTS studies by carrying out experiments on the drug substance and probe formulations. A probe formulation is the initial preliminary formulation for the sample drug which is then studied in order to determine the final optimal formulation. Assuming the reaction kinetics can be modeled with the Arrhenius equation, degradation kinetics studies may be accelerated by conducting them at elevated temperatures. Generally, reaction kinetics are doubled with each 10° C. increase. FIG. 1 generally demonstrates the time savings afforded by conducting degradation reactions at elevated temperatures.

The accelerated studies may be conducted using isothermal reactions (same temperature throughout the reaction period) or nonisothermal reactions (temperature programming during reaction period). Reaction kinetics studies typically involve the collection and analysis of a large number of samples obtained at regular time intervals. A number of samples are evaluated over a predetermined time period by selectively removing samples at timed intervals and then conducting various tests to evaluate the reaction kinetics of the drug product over the entire time period of the study.

Traditionally, reaction kinetics have been studied under isothermal conditions and rate constants have been measured at multiple temperatures. As an example, the data for a first-order reaction can be fitted or modeled with a differential rate equation in which the decrease in the parent sample (e.g., a drug) ($-dC/dt$) is directly proportional to the concentration of the sample at time t (Equation 1: $-dC/dt=kC$) where k is the rate constant, and C is the concentration of the parent sample at time t. In studying reaction kinetics, reaction rates may be predicted at different temperatures using the Arrhenius equation (Equation 2: $k=Ae^{-E/RT}$) where A is the frequency of molecular collisions, E is the activation energy, R is the gas constant, and T is the absolute temperature. Typically, experimental data is generated from three or more temperatures in order to achieve these results.

Alternatively, equivalent rate data (i.e., the ability to calculate rate constants at any temperature) can be obtained in one experiment in which a temperature program is used. The resulting data is fit with a rate equation that contains terms for temperature and the concentration of the drug. Thus, for a first-order reaction, Equations 1 and 2 can be combined to give the following Equation 3: $-dC/dt=(Ae^{-E/RT(t)})C$ where the temperature, T(t), is now a function of time. Various temperature functions have been studied and are summarized in Table 1.

TABLE 1

Nonisothermal models used for degradation kinetics data

| Program | Model | Reference[1] |
|---|---|---|
| Logarithmic | $\frac{1}{T_0} - \frac{1}{T(t)} = 2.303 * b\log(1+t)$<br>wherein b is the scaling factor. | Rogers, A. R., An Accelerated Storage Test with Programmed Temperature Rise. J. Pharm. and Pharmacol., 1963. 15: p. 101t–105t; Tucker, I. G., An assessment of a logarithmic nonisothermal storage test. Drug Dev. Ind. Pharm., 1981. 7(2): p. 231–246; Rosenberg, L. S., et al., Nonisothermal methods for stability prediction. J. Parenter. Sci. Technol., 1986. 40(4): p. 164–168; Cole, B. R. and L. Leadbeater, A critical assessment of an accelerated storage test. J. Pharm. Pharmacol., 1966. 18: p. 101–111; Anderson, R. A. and M. Campbell, Simple nonisothermal method for predicting stability of pharmaceuticals. Australas. J. Pharm., 1971. 52(623): p. S81–S83. |

TABLE 1-continued

Nonisothermal models used for degradation kinetics data

| Program | Model | Reference[1] |
|---|---|---|
| Reciprocal | $\frac{1}{T(t)} = \frac{1}{T_0}; -at$<br>wherein a is the reciprocal heating constant | Zhan, X., et al., Computer-controlled heating system and new computation for reciprocal heating stability experiment. Int. J. Pharm., 1995. 115(2): p. 167–173; Eriksen, S. P. and H. Stelmach, Single-step stability studies. J. Pharm. Sci., 1965. 54(7): p. 1029–1034. |
| Linear | $T(t) = bt + T_0$;<br>wherein b is the heating pump | Kipp, J. E. and J. J. Hlavaty, Nonisothermal stability assessment of stable pharmaceuticals: testing of a clindamycin phosphate formulation. Pharm. Res., 1991. 8(5): p. 570–575; Junnarkar, G. H. and S. Stavchansky, Isothermal and nonisothermal decomposition of famotidine in aqueous solution. Pharm. Res., 1995. 12(4): p. 599–604; Zhan, X., G. Yin, and B. Ma, New heating controller and computation for linear heating stability experiment. Int. J. Pharm., 1995. 115(2): p. 161–166; Rosenberg, L. S., et al., Nonisothermal methods for stability prediction. J. Parenter. Sci. Technol., 1986. 40(4): p. 164–168; Zoglio, M. A., et al, Linear nonisothermal stability studies [of pharmaceuticals]. J. Pharm. Sci., 1968. 57(12): p. 2080–2085; Kay, A. I. and T. H. Simon, Use of an analog computer to simulate and interpret data obtained from linear nonisothermal stability studies. J. Pharm. Sci., 1971. 60(2): p. 205–208; Okusa, N., Prediction of the stability of drugs. IV. Prediction of the stability by a multilevel nonisothermal method. Chem. Pharm. Bull., 1975. 23(4): p. 803–809; Tucker, I. G. and W. R. Owen, Estimation of all parameters from nonisothermal kinetic data. J. Pharm. Sci., 1982. 71(9): p. 969–974; Waltersson, J. O. and P. Lundgren, Nonisothermal kinetics applied to pharmaceuticals. Acta Pharm. Suec., 1982. 19(2): p. 127–136. 21. Ahlneck, C. and P. Lundgren, Methods for the evaluation of solid state stability and compatibility between drug and |
| (continued) | | Ahlneck, C. and P. Lundgren, Methods for the evaluation of solid state stability and compatibility between drug and excipient. Acta Pharm. Suec., 1986. 22(6): p. 305–314. |
| Stepped linear temperature | 0.3° C. step every 3 hours | Edel, B. and M. O. Baltzer, Nonisothermal kinetics with programmed temperature steps. J. Pharm. Sci., 1980. 69(3): p. 287–290. |
| Linear followed by isothermal | Self explanatory | Zoglio, M. A., et al., Nonisothermal kinetic studies. III. Rapid nonisothermal-isothermal method for stability prediction. J. Pharm. Sci., 1975. 64(8): p. 1381–1383. |
| Linear up and down | Triangular ramping | Zhan, X., G. Yin, and B. Ma, Determination of Rate Order for Degradation of Drugs with Nonisothermal Stability Experiment. J. Pharm. Sci., 1997. 86(10): p. 1099–1104. |
| Uncontrolled | Self explanatory | Hodgson, S. C., et al., A student experiment in non-isothermal chemical kinetics. J. Chem. Ed., 1998. 75(9): p. 1150–1153. |

TABLE 1-continued

Nonisothermal models used for degradation kinetics data

| Program | Model | Reference[1] |
|---|---|---|
| Polynomial | $T(t) = T_0 + a_1 t + a_2 t + \ldots$ | Maulding, H. V., Jr. and M. A. Zoglio, Flexible nonisothermal stability studies. J. Pharm. Sci., 1970. 59(3): p. 333–337. |
| Power Function of time | $T(t) = T_0 + kt^n$ wherein k is a constant and n is from 1 to 5 | Yoshioka, S., Y. Aso, and Y. Takeda, Isothermal and nonisothermal kinetics in the stability prediction of vitamin A preparations. Pharm. Res., 1990. 7(4): p. 388–391; Yoshioka, S., Y. Aso, and M. Uchiyama, Statistical evaluation of nonisothermal prediction of drug stability. II. Experimental design for practical drug products. Int. J. Pharm., 1988. 46(1–2): p. 121–132. |
| Exponential Heating Model (a = constant 2-4) | $T(t) = T_0 - \dfrac{10 \ln\left\{1 - \left[1 - a^{T_0 - \frac{T_{final}}{10}}\right] \dfrac{t}{t_{final}}\right\}}{\ln a}$ | Zhan, X., et al., Exponential Heating in Drug Stability Experiment and Statistical Evaluation of Nonisothermal and Isothermal Prediction. J. Pharm. Sci., 1997. 86(6): p. 709–715. |

[1]All of the references listed in this table are expressly incorporated herein their entirety.

Once the activation energy (E) and the frequency factor (A) have been determined by fitting the data to a model such as Equation 3, then rate constants are calculated for various temperatures with the Arrhenius equation (Equation 2). Comparison studies with isothermal approaches have given nearly identical results (e.g., see the above-listed articles by Rogers; Kipp et al.; Junnarkar et al.; Zhan et al and Davis, A. R., Temperature as a variable during kinetic experiments. J. Phys. Chem., 1959. 63: p. 307–309; Lee, M. L., et al. Isothermal and nonisothermal decomposition of thymopentin and its analogs in aqueous solution. Pharm. Res., 1998. 15(11): p. 1702–1707, all of which are hereby incorporated by reference in their entirety.

In general, conducting isothermal or nonisothermal degradation reaction studies involves the following operations: (1) obtaining sufficient data points (usually 30–40) to obtain a good fit for the kinetics models; (2) running multiple reactions in parallel to complete the study in a reasonable time period; (3) programming desired temperature profiles; (4) programming sampling intervals; (5) maintaining solutions of the drug or samples of the drug substance under programmed temperatures; (6) removing samples of the reaction product mixtures at programmed intervals; (7) storing the samples at a low enough temperature to quench the reaction; (8) recording the actual block temperatures; (9) recording actual sampling times; and (10) analyzing the samples by techniques such as high pressure liquid chromatography (HPLC).

Analyses of samples using an HPLC apparatus can be performed in an automated fashion using commercially available instrumentation. Due to the large time interval between sampling (e.g., 12 hours) and the length of the study (e.g., up to 3 weeks or so) it would be inappropriate to dedicate one HPLC apparatus per reaction as this would be an ineffective allocation of resources. What is needed in the art and has heretofore not been available is a completely automated apparatus for studying chemical reaction kinetics and studying product distributions in pharmaceutical development and other settings. What is further needed is an apparatus which permits the user to independently program temperature profiles and sampling periods for each reaction block, thereby allowing parallel reactions which result in higher throughput and cost savings. The present invention satisfies these and other needs.

SUMMARY OF THE INVENTION

The present invention relates to an apparatus and a method for conducting degradation studies to determine the stability of a test compound, e.g., a drug. More specifically, the apparatus of the present invention allows for temperature programming and autosampling of reactions. Advantageously, the present apparatus permits the studies to include both isothermal and nonisothermal reactions which are performed in one single apparatus.

In one embodiment according to the present invention, the apparatus includes at least one hot reaction block for heating a predetermined amount of reaction vessels at elevated temperatures over a reaction time period and at least one cold reaction block for storing one or more of the reaction vessels after they are removed from the hot reaction block for subsequent analysis. Each hot reaction block subjects the reaction vessels to varying reaction parameters depending upon the precise study requirements and generally subjects the reaction vessels to elevated temperatures over a period of time. Each cold reaction block subjects the reaction vessels to temperatures which are low enough that they quench the chemical reaction and thus permit the vessels to be safely stored for subsequent analysis. The apparatus also includes a robotic device for moving sample reaction vessels from the hot reaction block to the cold reaction block at a specific time period and also a temperature controller is used to regulate the temperatures of the hot and cold reaction blocks. A user interface which includes an operating system permits the user to input certain select information and also serves to log data. The present invention permits the entire preparation and testing process to be fully automated so that all of the labor intensive tasks prior to analyzing the sample vessels are conducted in a fully automated manner. In addition, all of the components of the present apparatus are preferably integrated and therefore excellent control over experimental parameters is achieved.

The present invention provides a number of advantages over conventional devices and processes used to perform chemical reaction kinetics studies. For example, the present invention allows for continuous data logging which provides a convenient audit trail for the analysts. This feature also complies with standard operating procedures to ensure that the actual temperatures of a study follow user defined temperatures. Each sample vessel may represent a single data point and thus, no cross contamination between samples during the experiment can occur, in contrast to sampling from a single reaction vessel which suffers from such a disadvantage. The hot and cold reaction blocks are preferably designed in view of this goal and therefore permit sample vessels to be easily inserted and removed as the study progresses. The preferred reaction vessels are ideal for these type of reaction studies because they can be loaded directly onto a HPLC apparatus for analysis after being removed from one of the hot and cold reaction blocks.

The present invention is more efficient than manual methods for performing chemical reaction kinetics studies because after the apparatus is setup by the user, multiple operations are carried out in an automated fashion. The apparatus of the present invention also provides the ability to run multiple reactions in parallel to allow higher throughput and cost savings.

Another advantage of the present invention is the ability to input a temperature and sampling versus time program for each individual reaction block. This provides greater flexibility for the user because non-isothermal and isothermal reactions, for example, can be run in parallel. The apparatus is designed to provide flexibility for unforeseen developments in degradation kinetics (i.e., temperature programs other than those listed in Table 1).

A further advantage of the apparatus of the present invention is that kinetics studies are extremely labor intensive and these instruments remove all of the redundant tasks as outlined above. Therefore the apparatus of the present invention provides an attractive system for drug development companies that are interested in reducing their workloads and timelines in getting a drug to market.

The kinetics apparatus of the invention, unlike prior devices, is designed to address the major operations involved in performing an accelerated degradation study. Because of the large interval between sampling and the length of the study, HPLC analyses are not incorporated in one embodiment. However, provisions were made for the optional use of HPLC autosampler vials as reaction vessels.

BRIEF DESCRIPTION OF THE DRAWINGS

The foregoing and other features of the present invention will be more readily apparent from the following detailed description and drawings of illustrative embodiments of the invention in which.

DETAILED DESCRIPTION OF THE INVENTION

Figure 1:
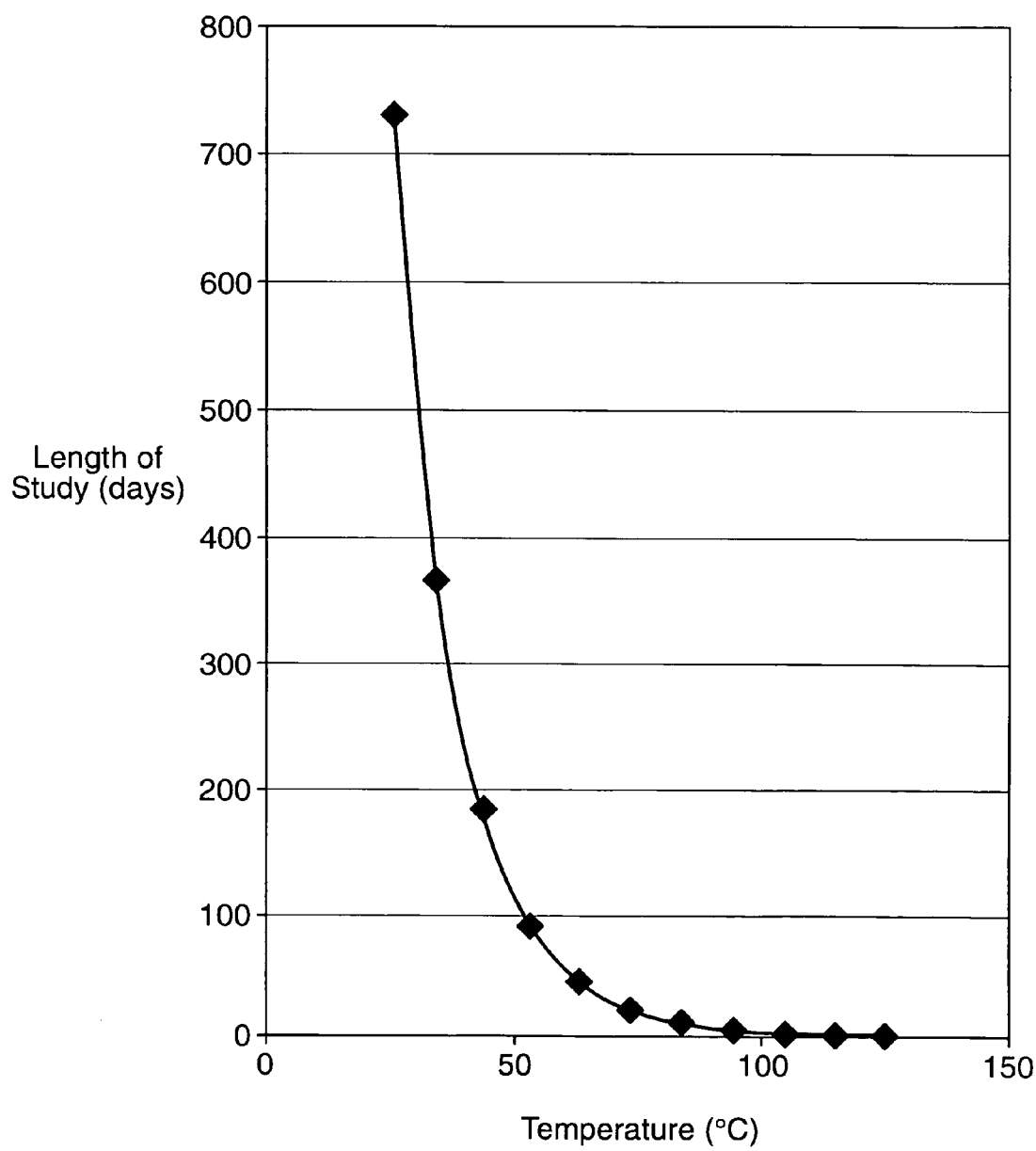
FIG. 1 is a graph illustrating the length of degradation studies as a function of temperature of the reaction.
Figure 2:
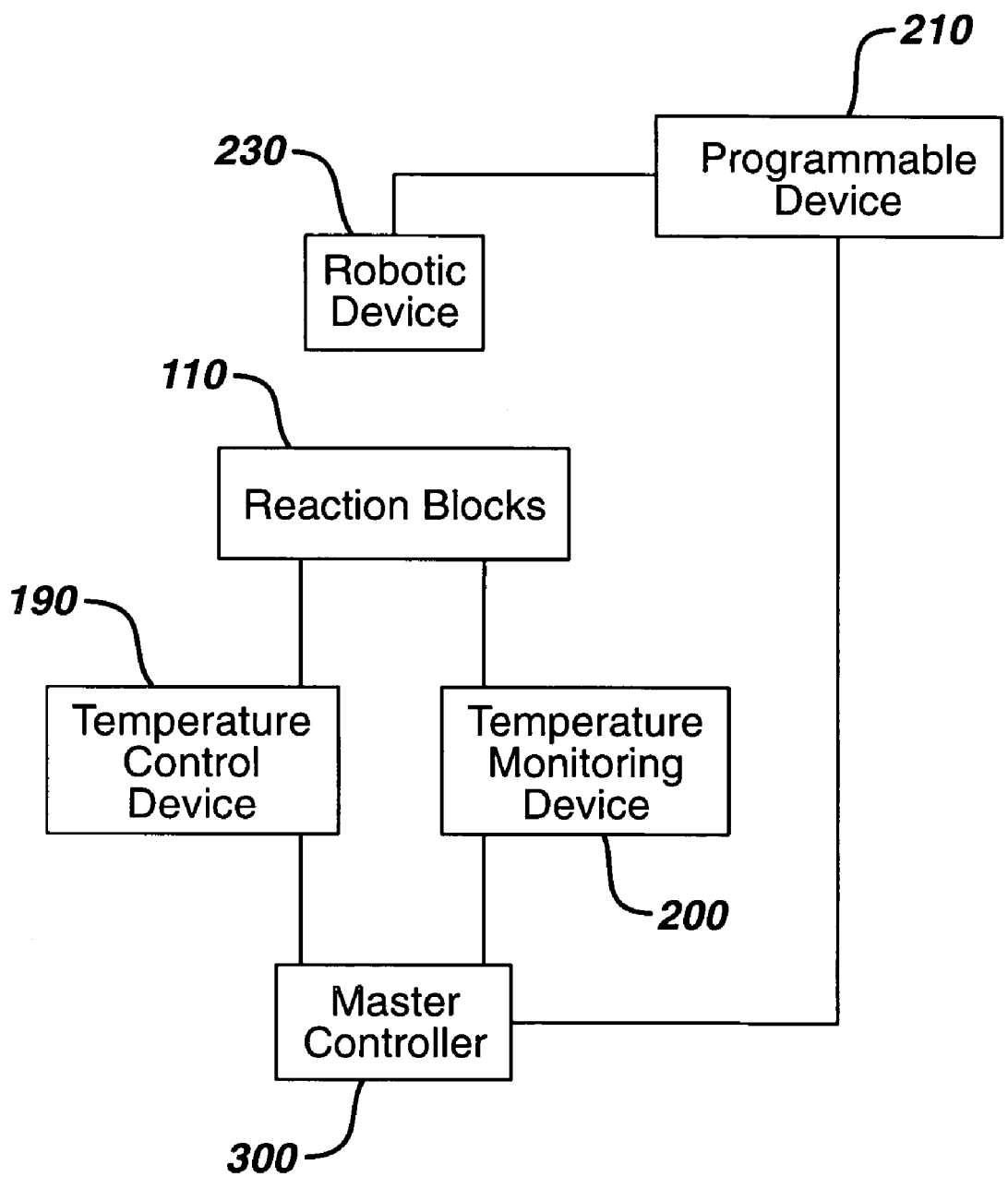
FIG. 2 is a block diagram illustrating the major components of an automated apparatus for performing chemical reaction kinetics studies according to the present invention.

Referring now to FIGS. 2–7, an apparatus for performing chemical reaction kinetics studies according to the present invention is illustrated and generally indicated at 100. The apparatus 100 is designed to conduct isothermal or nonisothermal degradation reaction studies and is designed to perform operations 1 through 9 set forth hereinbefore on pages 7–8. More specifically, the apparatus 100 collects a sufficient number of data points so that a good fit for a kinetics model is obtained for one or more chemical reaction studies over a predetermined period of time. As will be described in greater detail hereinafter, a user may program the apparatus 100 with desired temperature profiles and sampling intervals so that the samples, e.g., solutions or substances, are maintained under programmed temperatures and for programmed time intervals. At programmed intervals, the apparatus 100 removes the samples from a first stage and stores the samples under predefined conditions, while corresponding temperature and time information is recorded throughout the study.

The apparatus 100 generally includes a plurality of multi-temperature reaction blocks 110. Multi-temperature reaction blocks 110 are commercially available from a number of different sources and are designed to subject samples to demanding chemical reaction conditions, while being programmable so that the temperature of the blocks 110 may be varied over time if desired. The reaction blocks 110 of the present invention are divided into one or more hot reaction blocks 120 and one or more cold reaction blocks 130. In one embodiment, the hot and cold reaction blocks 120, 130 are formed of removable blocks with openings 140, 150, respectively, formed therein to accommodate a predetermined number of reaction vessels 160. The reaction vessels 160 may be selected from any number of types of reaction vessels that are available so long as the vessels 160 are suitable for use under the precise reaction conditions that exist in the blocks 120, 130 during the particular study.

The openings 140, 150 are designed so as to either accommodate a specific type of reaction vessel 160 or the openings 140, 150 are dimensioned to receive reaction vessels 160 having standard dimensions. For example, the reaction vessels 160 may be standard 2 ml HPLC autosampler vials, e.g., vials marketed under the name Chromacol 2-CV having caps, e.g., sealed silicon Teflon® crimp caps marked under the name Chromacol 11-AC-ST15. Alternatively, the reaction vessels 160 may be standard 2 ml sealed glass ampules. Different vials have different maximum temperature limits which will determine which type of vials may be used in any particular application. For example, the standard HPLC autosampler vials may be used in applications where the temperature is about 100° C. or less, while standard glass ampules may be used with temperatures up to about 200° C.

It will be understood that the reaction vessel 160 may hold a predetermined number of melting point capillary tubes (not shown) which each holds one sample compound to be subjected to the degradation study and later testing. In other words, a number of samples (e.g., drugs) may be tested at one time by disposing the tubes in each of the reaction vessels. This results in reaction data for each of the multiple samples being gathered when each reaction vessel is transferred at the specific interval. Advantageously, this capability of the apparatus 100 increases the efficiency and versatility of the apparatus 100 in performing kinetics studies.

The blocks 120, 130 are preferably constructed of a material which is extremely resistant to corrosive reagents and organic solvents, thereby permitting the blocks 120, 130 to demonstrate outstanding chemical compatibility and heat resistance. The properties make the blocks 120, 130 particularly suited for the demanding chemical reaction conditions which are experienced during reaction studies. In one exemplary embodiment, the blocks 120, 130 are formed of aluminum. Each of the blocks 120, 130 has a body 122, 132, respectively, which defines an internal cavity (not shown). The blocks 120, 130 are heated or cooled to desired temperatures using conventional means including but not limited to placing the blocks 120, 130 on a heat transfer surface and it is also within the scope of the present invention that the heating and cooling may be accomplished by filling the internal cavities of each block with a circulating fluid and then controlling the temperature thereof.

Each of the blocks 120, 130 is disposed within a housing 124, 134, respectively, which is associated with either a heating device 170 or a cooling device 180. More specifically, one hot reaction block 120 is disposed within one housing 124 associated with one or more heating devices 170 and one cold reaction block 130 is disposed within one housing 134 associated with one or more cooling devices 180. Each of the housings 124, 134 includes an opening 125 which receives one hot reaction block 120 and one cold reaction block 130, respectively.

Each of the devices 170, 180 maintains the temperature of the blocks 120, 130, respectively, at desired programmed temperatures and the devices 170, 180 along with the blocks 120, 130 are capable of providing very low temperature differentials, e.g., less than 1° C., across the regions of the blocks 120, 130. Each of the blocks 120, 130 is thus fairly uniformly heated or cooled across all of the regions thereof. In one embodiment, the heating device 170 is a heater which provides uniform heating of the reaction vessels 160 disposed within the hot reaction block 120. For example, the heating device 170 may be a silicon rubber heater having an etched foil element for providing the desired even heating. One such heater 170 is commercially available from Watlow Controls under the trade name F030050C7-A001B. In one embodiment, each hot reaction block 120 is placed on the heater 170 which is in the form of a planar heat transfer surface. The heat is uniformly transferred from the surface to the hot reaction block 120.

The cooling device 180 acts to uniformly cool the reaction vessels 160 disposed within the cold reaction block 130. A suitable cooling device 180 is an electric cooler, such as a device commercially available under the trade name ST3353-02 from Marlow Industries. In one embodiment, the cooling device 180 includes a planar heat transfer surface on which the cold reaction block 130 is placed. Power for the cooling device 180 is preferably provided by a switching regulated (12 VDC/4.1 amp) power supply, e.g., a device from Acopian marketed under the trade name 12WB410. Preferably, the blocks 120, 130 are insulated with a suitable insulating material so that the blocks 120, 130 either retain the heat or maintain the cooled temperatures within the interior cavity of each of the blocks 120, 130. One suitable type of insulating material is a one inch thick melamine white foam, e.g., foam marketed under the designation 86145K54 by McMaster Carr.

The apparatus 100 also includes a temperature control device 190 and a temperature monitoring device 200 which are both used in conjunction with each of the blocks 120, 130. One or more of the devices 190, 200 may be incorporated into the respective housings 124, 134. The temperature monitoring device 200 serves to monitor the temperature within one of the blocks 120, 130 to a high degree of precision. For example, the temperature monitoring device 200 may comprise a temperature sensor which detects the temperature and then generates a representative signal and more particularly, the temperature monitoring device 200 is a high precision resistance temperature detector (RTD). As is known, an RTD is a sensor that uses the resistance temperature characteristic to measure temperature. There are two basic types of RTDs: a wire RTD, which is usually made of platinum, and a thermistor, which is made of a semiconductor material. The wire RTD is a positive temperature coefficient sensor only, while the thermistor can have either a negative or positive temperature coefficient. One suitable RTD for use in the apparatus 100 of the present invention is a high precision detector which is commercially available from Watlow Controls under the trade name S80-100204.

The temperature control device (controller) 190 serves to control the temperatures of the blocks 120, 130. A great number of temperature control devices 190 are available and come in different configurations, such as a single loop, dual loop or multi loop controllers. In one embodiment, the temperatures of the blocks 120, 130 are controlled using a dual loop temperature controller commercially available from Watlow Controls under the trade name 999D-22CC-AURG. The controller 190 provides a digital signal to regulate the power supplied to the heating and cooling devices 170, 180, respectively, via solid-state relays or the like, e.g., relays available from Grayhill under the trade names 70S2-04-B-06-N (associated with the heating device) and 70S2-01-A-05-N (associated with the cooling device). The temperature controller 190 is designed to hold the blocks 120, 130 to within 0.1° C. of a user defined (inputted) temperature. The standard deviation of temperature between the reaction vessels 160 within one of the blocks 120, 130 is within acceptable experimental limits based on experimental protocol, experiment guidelines, product specifications and product literature. For example, the standard deviation of temperature between the reaction vessels 160 spaced throughout one reaction block 110 was about 0.3° C. during recent tests of the apparatus 100 of the present invention.

The apparatus 100 also includes a programmable device 210 (referred to also as an "autosampler") for automating the apparatus 100 and more specifically, for transferring sample reaction vessels 160 from one hot block 120 to one cold block 130. The automated device 210 is designed to move one or more reaction vessels 160 at a specified, predefined time during the chemical kinetics study so that the chemical reaction is studied by analyzing the sample within each of the reaction vessels 160 with each reaction vessel 160 being a single data point used to obtain a good fit for the selected kinetics model. As will be described in greater detail hereinafter, the automated device 210, along with the temperature controller 190 and the temperature monitoring device 200, are all preferably in communication with a master controller 300.

Figure 3:
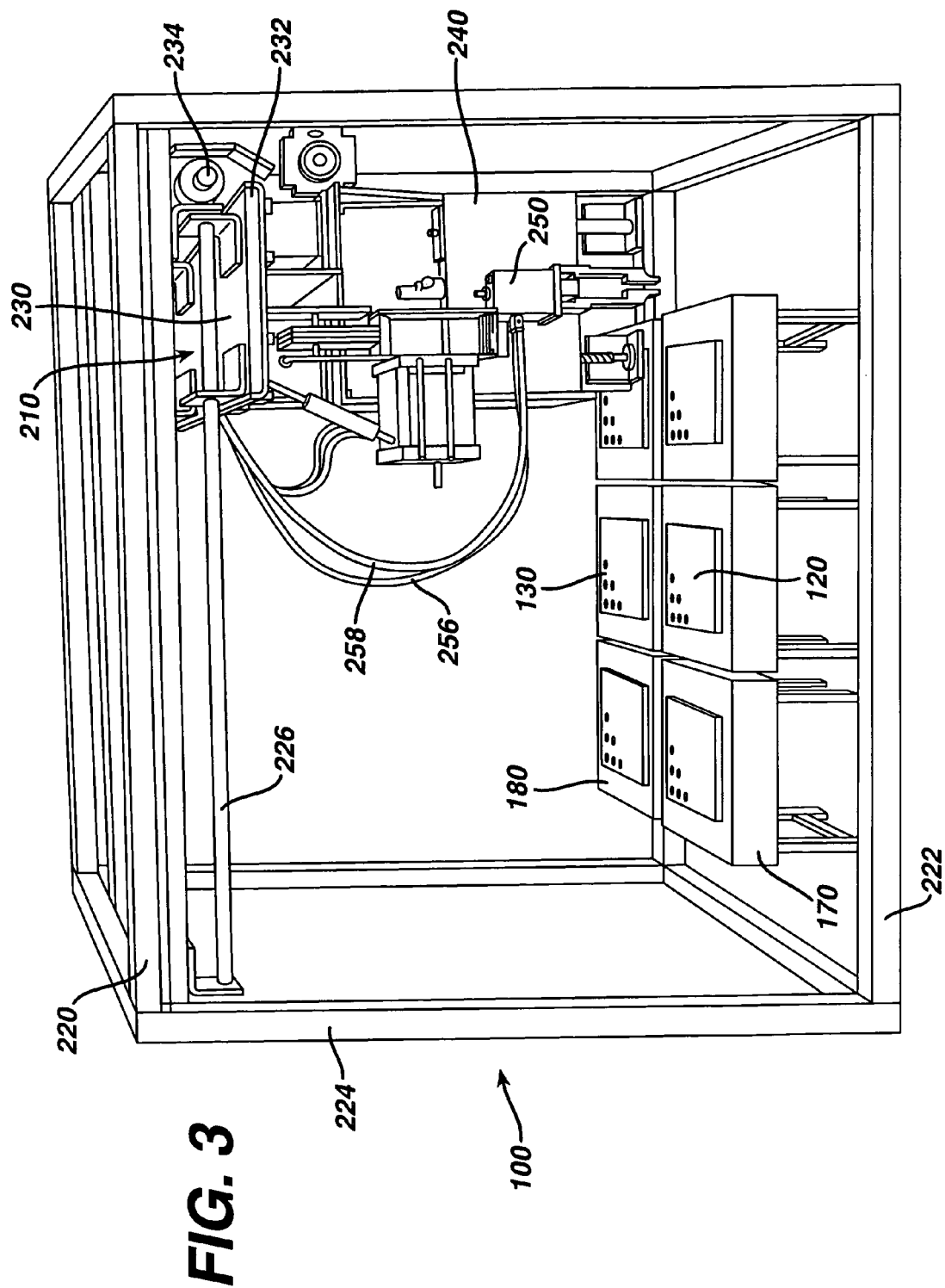
FIG. 3 is a perspective side view of the apparatus according to one embodiment of the present invention.

As best shown in FIG. 3, the device 210 includes a frame 220 which permits the device 210 to be moved to a desired location relative to the blocks 120, 130 so that one or more reactions vessels 160 may be moved from one location to another using the device 210. In the exemplary embodiment, the frame 220 is generally of a box-like configuration having horizontal members 222 and vertical members 224. The first blocks 120, 130 are generally disposed within the frame 220 and the frame 220 also includes one or more tracks 226 which permit a robotic device 230 to move three dimensionally relative to the frame 220. In other words, the tracks 226 are disposed so that the robotic device 230 is permitted to move along three axises (x, y, and z) such that the robotic device 230 may be properly positioned relative to any of the blocks 120, 130, thereby allowing the robotic device 230 to grasp one of the reaction vessels 160 disposed therein for repositioning thereof.

The robotic device 230 includes a main unit 240 which rides along the one or more tracks 226 and is designed to be positioned, upon command, to a desired coordinate point at a predefined period of time so that the reaction vessel 160 may be grasped and removed from the hot block 120 and then repositioned within the cold block 130 or moved from the cold block 130 to another location, such as an HPLC instrument. Any number of programmable robotic devices 230 may be used in the practice of the present invention, including laboratory robotic devices which are referred to as robotic workcells. One such robotic device 230 that is suitable for use in the present invention is a three axis robotic workcell commercially available from Arrick Robotics under the trade name RW-18b-3-Axis. Each axis on which the robotic device 230 is free to travel contains components which permit the main unit 240 to be moved with precision to a desired coordinate location within the frame 220. For example, the robotic device 230 may include a number of stepper motors 232 and a number of pulley reducers 234 on each axis of movement so as to permit the main unit 240 to be precisely moved to within 0.002 inches of the predefined coordinate location, e.g., a position of one of the reaction vessels 160. The power supply for the stepper motors 232 may be incorporated into the robotic device 230 or may be incorporated into other components or even into the master controller 300.

It will be appreciated that movement of the robotic device 230 along the x and y axises causes the main unit 240 be positioned over one of the reaction vessels 160 disposed within one of the blocks 120, 130. Movement of the robotic device 230 along the z axis causes the main unit 240 to be moved either toward or away from the reaction vessel 160.

The main unit 240 includes a gripping mechanism 250 which acts to grip one of the reaction vessels 160 which is targeted for transfer from the hot block 120 to the cold block 130. As best shown in FIGS. 1 and 3, the gripping mechanism 250 is mounted using conventional techniques and has a pair of spaced, opposing adjustable fingers 252, 254 for selectively grasping one reaction vessel 160 in response to receiving control signals. The fingers 252, 254 are configured such that they have a complementary shape with respect to the reaction vessel 160. This permits the fingers 252, 254 to securely grip and retain a top section of one reaction vessel 160 upon actuation of the gripping mechanism 250. The fingers 252, 254 may be actuated using any number of suitable techniques and in one embodiment, the gripping mechanism 250 is a pneumatic gripper commercially available from SMC Pneumatics under the trade name MHQ2-16D.

In one exemplary embodiment, the gripping mechanism 250 is operated by toggling a predetermined pressure, e.g., 20 p.s.i., between a first line 256 and a second line 258. The first line 256 opens the fingers 252, 254 of the gripping mechanism 250 when a pressure is applied to the first line 256, while the second line 258 is vented and conversely, the fingers 252, 254 of the gripping mechanism 250 are closed by applying a pressure to the second line 258 while the first line 256 is vented. The first and second lines 256, 258 may be regulated using any number of devices (not shown) and in one embodiment, a solenoid is used to regulate the pressure within each of the first and second lines 256, 258. Upon being activated, the solenoid either pressurizes or vents one of the first and second lines 256, 258, thereby causing the gripping mechanism 250 to open or close depending upon which of the lines 256, 258 is pressurized and which of the lines 256, 258 is vented. Pressure is applied to the first and second lines 256, 258 by connecting the lines 256, 258 to a pneumatic source (not shown) which applies pressure to the lines 256, 258 upon command. The pneumatic source is preferably associated with the robotic device 230 but may be a separate component and integrated with the robotic device 230.

The master controller 300 integrates all of the individual components of the apparatus 100 to advantageously permit the entire sample transfer and data logging operations to be done by a single automated apparatus 100. The apparatus 100 thus provides a chemical kinetics instrument that performs the labor intensive tasks of conducting degradation reactions. By integrating all of the components into one instrument (apparatus 100), excellent control over the experimental parameters is achieved. The master controller 300 is in communication with each of the temperature control device 190, the temperature monitoring device 200 and the automated device 210 so that the user may control a complete degradation study, including programming the parameters thereof, using the centralized master controller 300.

The master controller 300 is programmable and contains software which, along with other components, generates command signals for operating the apparatus 100 and collecting and storing data generated during the study. The master controller includes a user interface 310 which permits the user to program certain parameters relating to conducting a particular degradation study or the like where data is logged over a certain time period. For example, a computer program may be written in a particular form, such as LabVIEW 5.1®, which allows the user to input the desired temperature and exposure time for each reaction vessel 160 disposed in one of the reaction blocks 120. The user interface 310 thus includes an operating system which permits the user to input certain information and also serves to collect and log data as will be described hereinafter. The operating system also serves to instruct and control the operation of the device 210 and more specifically, controls the entire reaction vessel transfer process where the reaction vessels 160 are individually transferred from the hot block 120 to the cold block 130 at predefined interval times.

Figure 6:
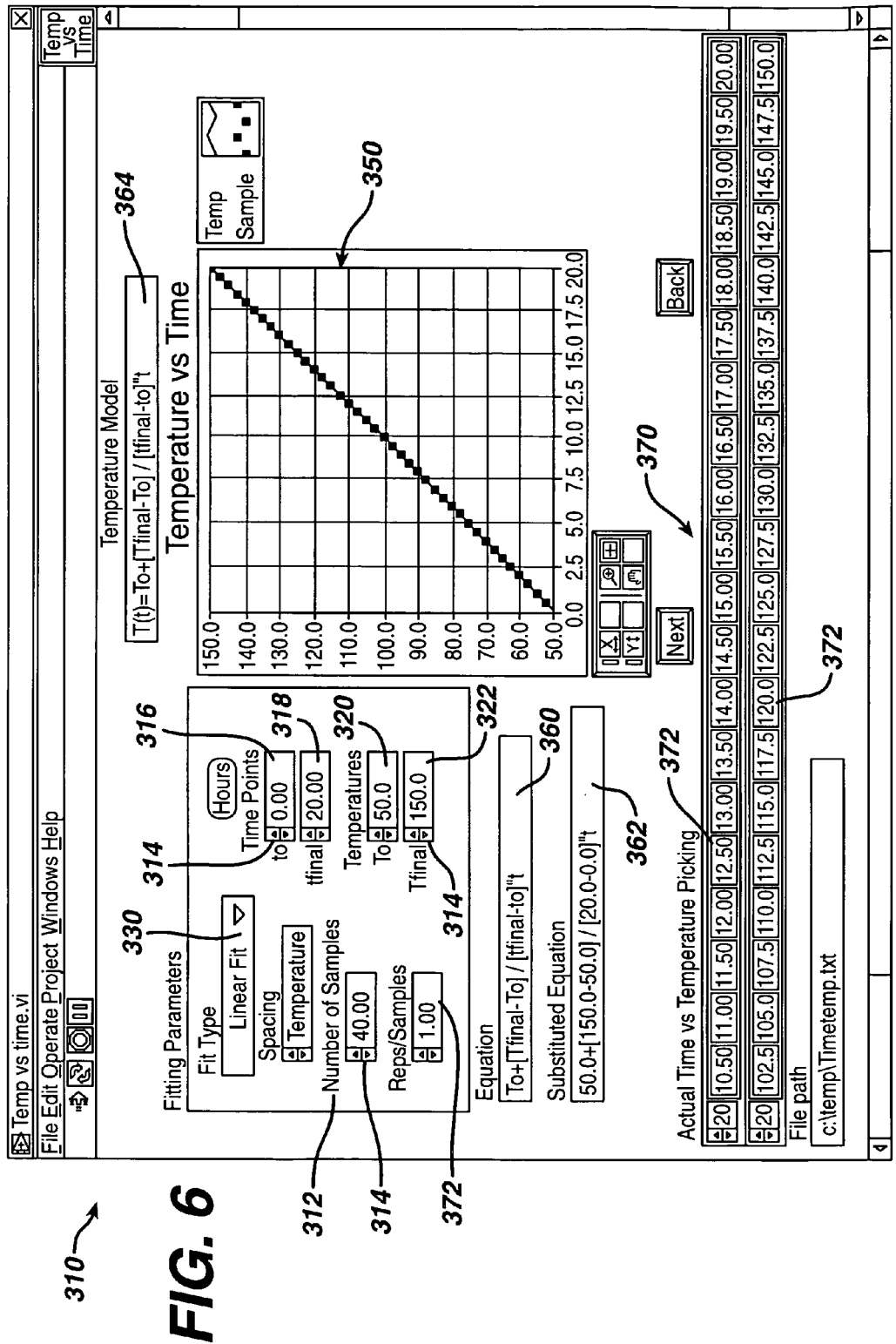
FIG. 6 is a graphical display screen of a user interface of the apparatus.

One exemplary user interface 310 is shown in FIG. 6. This exemplary user interface 310 permits the user to at least enter the number of samples, a desired temperature profile, a sample interval, and a model for fitting the data points into a representative profile. More specifically, the user enters a first input which represents the number of samples for use in the study and a first input display 312 shows the presently selected number of samples. The user may input the number of samples into the master controller 300 by using up and down arrow keys 314. In addition, the user may manually enter the desired number of samples using a keyboard (not shown). In this instance, the user may simply highlight the display 312 using conventional techniques and then enter the number of samples which will be used in a particular study.

A second input ($t_0$) represents an initial time point for the study to begin at and a third input ($t_{final}$) represents an ending time point for the study. Thus, the time period ($t_0$) to ($t_{final}$) represents the inputted time profile for any particular study. A second input display 316 shows the presently selected initial time point ($t_0$) and a third input display 318 shows the presently selected ending time point ($t_{final}$). The user may enter the second and third inputs using up and down arrow keys 314 associated with the second and third input displays 316 and 318 or the user may manually enter these inputs using other conventional techniques. The user interface 310 may be programmed so that the incremental change of each of the second and third inputs may be varied by the user. For example, the user may desire for the time inputs to increase or decrease in small increments, e.g., 0.5 seconds, or the user may desire for the time inputs to increase or decrease in larger increments, e.g., 10 minutes when using the up and down arrow keys 314.

A fourth input ($T_0$) represents an initial temperature for the study to begin at and a fifth input ($T_{final}$) represents an ending temperature at which the study concludes. Thus, the temperature range ($T_0$) to ($T_{final}$) represents the inputted temperature profile for any particular study. A fourth input display 320 shows the inputted initial temperature ($T_0$) and a fifth input display 322 shows the inputted ending temperature ($T_{final}$). The user may enter the fourth and fifth inputs using up and down arrows keys 314 associated with the fourth and fifth input displays 320 and 322 or the user may manually enter these inputs using other techniques. As with the time points, the user interface 310 may be programmed so that the incremental change of the fourth and fifth inputs may be varied by the user.

The user also enters a model fit which will be used to map the collected data and form a representative temperature vs. time graph. A menu window 330 permits the user to enter the desired model fit and in one exemplary embodiment, the user selects the model fit using a pull-down menu display. Any number of model fits that are used in kinetics studies may be used. The selected model fit program is shown in the window 330. Examples of the types of model fit programs which may be selected by the user are listed in Table 1, e.g., logarithmic, reciprocal, linear, exponential, etc. While Table 1 lists programs for use when a nonisothermal temperature model has been selected, it will be understood that some of these programs or other suitable programs may be selected when an isothermal temperature model is selected. In FIG. 6, the user has selected a linear program as illustrated in the window 330. As is the case in FIG. 6, the user has selected a nonisothermal run since the fourth and fifth inputs are not the same temperature. If the user had desired to run an isothermal study, the fourth and fifth inputs would be the same temperature.

This results in a linear temperature vs. time graph being generated plotting the various data points representing specific transfers, as is shown in the display screen 350. The display screen 350 displays the appropriate coordinates on the x and y axises of the linear graph based upon what the user has inputted for the second, third, fourth, and fifth inputs. For example, in this exemplary embodiment, the user has selected a temperature profile which begins at 50.0° C. and ends at 150° C. and a time period beginning at 0.0 hours and ending at 20.00 hours. Thus, these values are the starting and ending points along the respective x and y axises.

The user interface 310 also preferably has other windows for displaying information to the user. For example, an equation window 360 and a substituted equation window 362 are provided for displaying the primary equation and the secondary equation that are being used to generate the graphical representation (the fit of the collected data) shown in the display screen 350. In other words, once the user has selected the type of model fit in window 330 that is to be used and the program that is to be used for fitting the collected data, the corresponding primary and substituted equation are shown in the windows 360, 262. For example, in this instance, the user has selected a linear program fit as shown in window 330 and therefore the primary equation shown in window 360 is one which is linear in nature and is designed to generate a linear graph by applying the collected data points to the primary equation. The substituted equation shown in window 362 is simply the primary equation with the first, second, third and fourth inputs incorporated therein. Thus, the linear graph shown in display 350 is generated by using the substituted equation with the data collected during the study being inserted therein to generate data points. A temperature model window 364 may also be provided and this simply displays the respective temperature/time equation based upon what model fit the user selected in window 330.

The user enters a sixth input which represents the number of samples (reaction vessels 160) which will be transferred at each transfer interval. The sixth input is displayed in a sixth input display 372 on the user interface 310. For example, if the user enters 2 as the sixth input, then each transfer action will involve moving 2 reactions vessels 160 for each transfer interval. FIG. 6 shows that, in this instance, the user has entered that only 1 reaction vessel 160 will be transferred at each transfer interval. In one embodiment, the master controller 300 calculates the time increments between transfer operations based on the number of samples, the sixth input and the inputted time profile by simply dividing the number of samples into the overall time period to arrive at uniform time increments between the transfers. For example, in the embodiment shown in FIG. 6, the user entered that 40 samples are to be transferred with only one reaction vessel 160 being transferred at each transfer interval. Thus, there will be 40 separate transfers. If the user had entered that 2 reaction vessels 160 are to be transferred at each transfer interval, there would only be 20 separate transfer intervals with 2 reaction vessels 160 being transferred at each transfer interval.

In another embodiment, the master controller 300 is configured so that the user may input a nonuniform transfer profile in which the amount of time between transfers of the reaction vessels 160 is not uniform. In this instance, the user may construct a transfer profile in which reaction vessels 160 are transferred at various predefined times. For example, the user may transfer a greater number of reaction vessels 160 at the beginning and/or the end of the study.

Furthermore, a display box 370 may be provided for graphically illustrating a plurality of blocks 372 which identify time intervals when reaction vessels 160 will be moved from the hot block 120 to the cold block 130 using the device 210. In the exemplary embodiment shown, there are 40 individual blocks 372 representing up to 40 samples that will be moved from the hot block 120 to the cold block 130 at predefined time intervals over a predetermined period of time. It will be appreciated that the program of the user interface 310 may be designed such that the boxes associated with the samples that have already been moved from the hot block 120 to the cold block 130 may be displayed differently in comparison to the blocks 372 associated with samples that have not been transferred from the hot block 120 to the cold block 130. As shown in FIG. 6, the top row of blocks 372 represents the x axis and indicates the last 20 transfers in terms of the time of each transfer. The bottom row of blocks 372 represents the y axis and indicates the last 20 transfers in terms of the temperature of each transfer.

The user interface 310 may provide other functions that the user may select, including conventional forward and backward buttons which permit the user to browse through multiple user interface pages.

Figure 7:
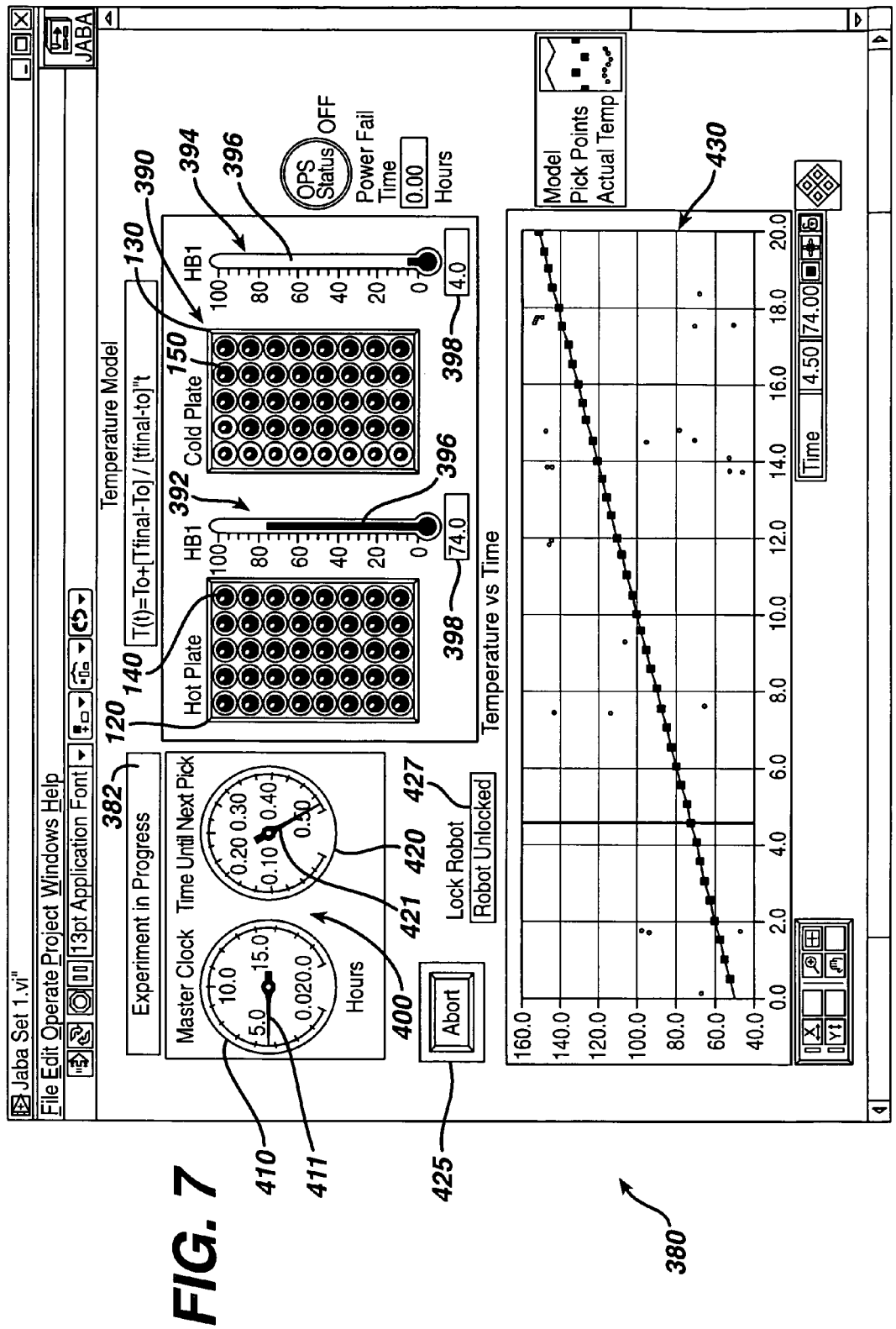
FIG. 7 is a graphical display of a master control panel of the apparatus.
Figure 8A:
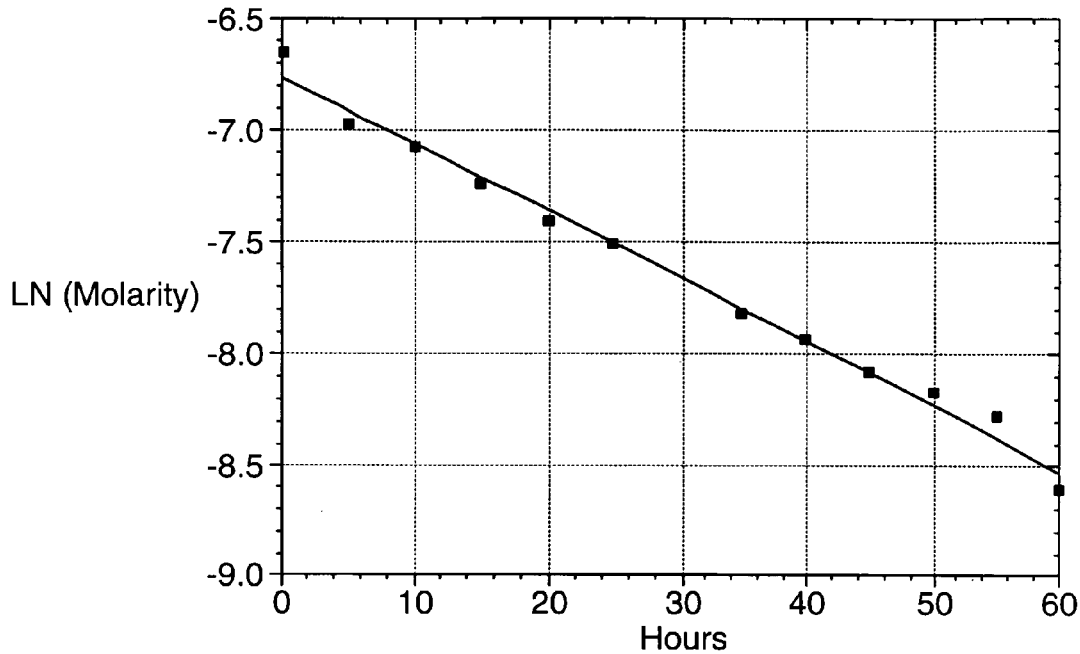
FIG. 8A is a graph of isothermal degradation at 85° C. of a model drug showing data points obtained for a reaction having a pH of 1.0.
Figure 8B:
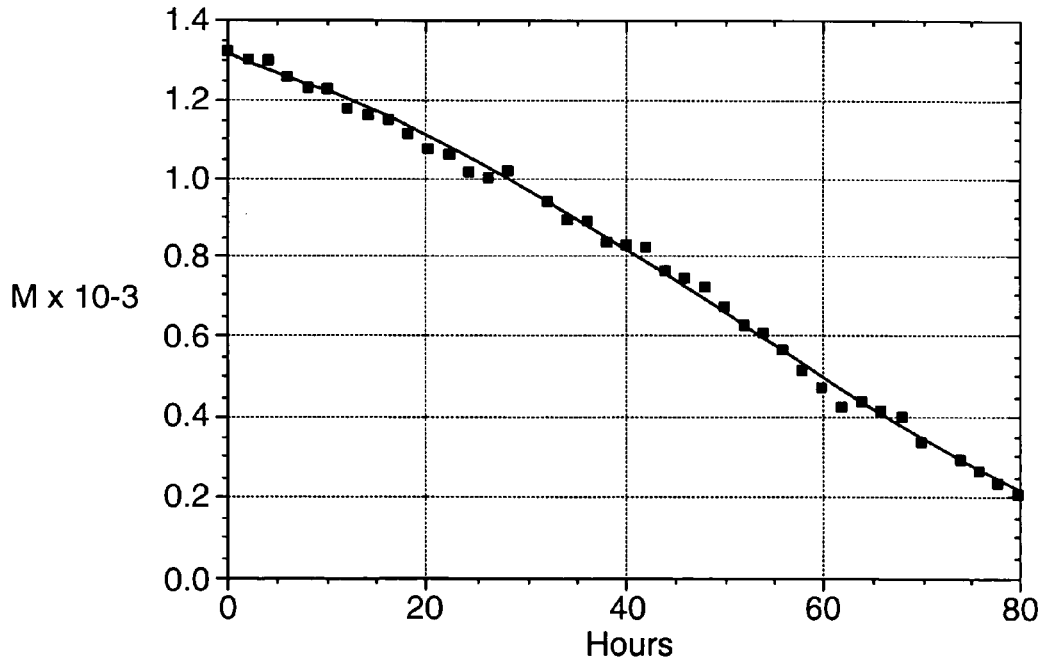
FIG. 8B is a graph of the degradation of the drug used in FIG. 8A under nonisothermal conditions where the temperature ranged from 50° to 100° C. over 80 hours for a reaction having a pH of 1.0.
Figure 9A:
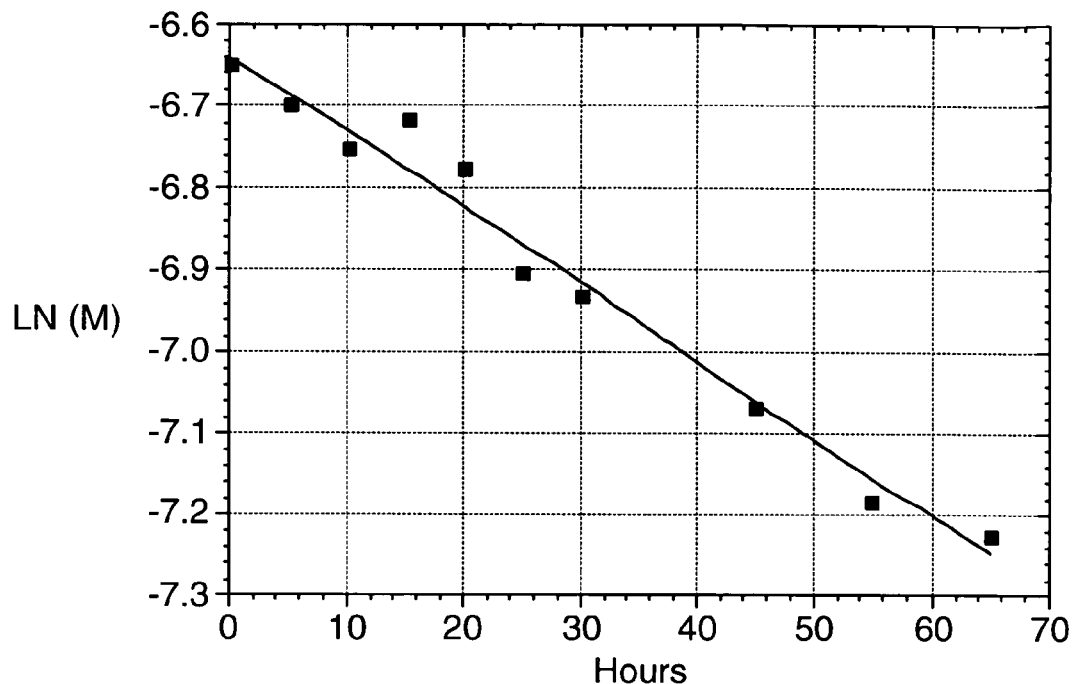
FIG. 9A is a graph of isothermal degradation at 85° C. of the model drug of FIG. 8 showing data points obtained for a reaction having a pH of 11.7.
Figure 9B:
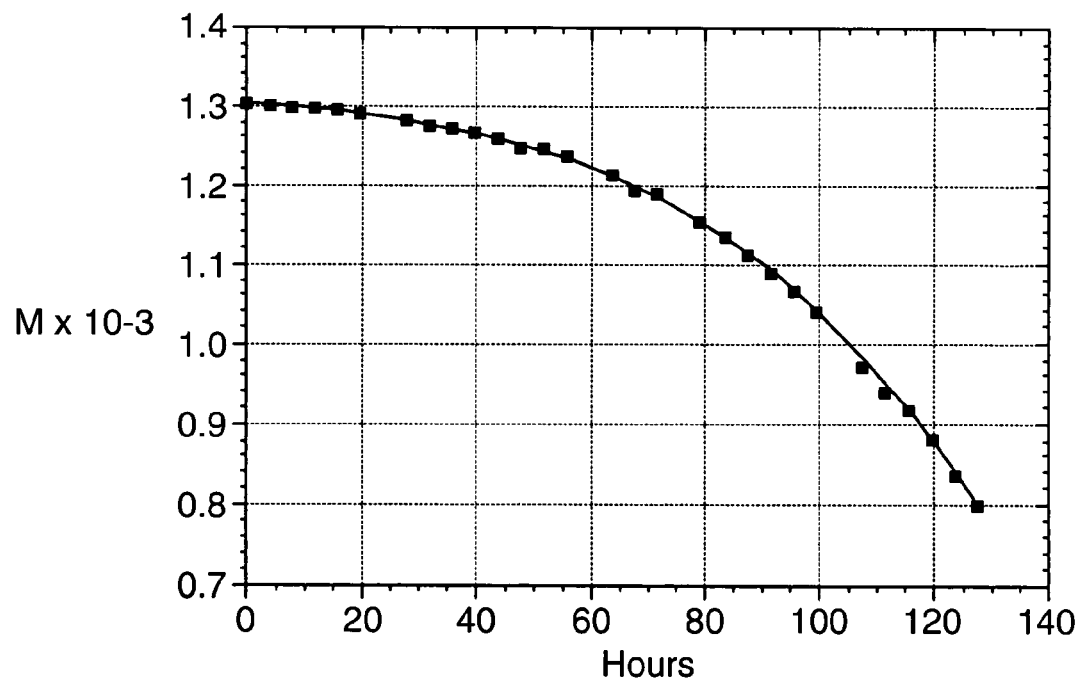
FIG. 9B is a graph of the degradation of the drug used in FIG. 9A under nonisothermal conditions where the temperature ranged from 50° to 100° C. over 160 hours for a reaction having a pH of 11.7.

As shown in FIG. 7, the operating system of the master controller 300 also includes a master control panel display screen 380 for providing certain information relating to the ongoing reaction study. For example, the control panel display screen 380 may have a window 382 which indicates whether a study is in progress or not. In addition, a graphical display of the blocks 120, 130 is shown in a display window 390. In the illustrated embodiment, one hot block 120 having 40 openings 140 and one cold block 130 having 40 openings 150 are shown. The precise location of the one or more reaction vessels 160 is shown by graphically marking the particular openings 140, 150 of the blocks 120, 130, respectively, that contain reaction vessels 160. For example, the particular openings 140, 150 that contain reactions vessels 160 may be highlighted as shown in FIG. 7. Next to each of the graphical displays of the blocks 120, 130 in the display window 390 is a thermometer 392, 394, respectively, which graphically displays the current temperature for each of the blocks 120, 130. For example, the thermometer 392 indicates the current temperature of the hot block 120 and the thermometer 394 indicates the current temperature of the cold block 130. In the exemplary embodiment, each of the thermometers 392, 394 has both a simulated thermometer representation 396 and a digital readout 398 of the measured temperature within the blocks 120, 130.

The master controller 300 also includes a clock display 400 which includes both a master clock display 410 and a count-down clock display 420. The master clock display 410 preferably has a digital readout which indicates the time profile of the current study. The time profile includes conventional markings which indicate various time increments and also includes a pointer 411 or the like for indicating how far within the time profile the current study is at. For example, FIG. 7 illustrates a study that has a total length of 20 hours and the present study is about 4.5 hours into the 20 hour total time frame as indicated by the pointer 411 (needle). As is typically the case with time displays, the pointer 411 moves in a clock-wise direction to indicate the passage of time and the progression of the study. The master clock display 410 thus indicates the relative time for the study.

The count-down clock display 420 indicates to the user the amount of time left before the next reaction vessel 160 is to be selected and moved from the hot block 120 to the cold block 130. The count-down clock display 420 thus permits the user to easily and conveniently determine when the next reaction vessel 160 will be moved from the block 120 to the block 130. The count-down display 420 is preferably a digital display and is generated based on the inputs of the user. More specifically, the count-down display will be based upon the specific time profile of the experiment and the number of samples. In the exemplary embodiment, the count-down display 420 is broken into time increments starting with 0.0 and extending to 0.50. Preferably, the count-down display 420 and the master clock display 410 have the same units of measurement and more specifically, the illustrated displays 410, 420 have increments measured in terms of hours. Thus, the illustrated count-down display 420 depicts that the time period between moving successive reaction vessels 160 is 0.50 hours. Once again, a pointer 421 or the like shows the precise current point in time on the display 420. Unlike, the pointer 411, the illustrated pointer 421 moves in a counter-clockwise direction.

It will also be appreciated that the master controller 300 may be configured so that the reaction vessels 160 are not transferred at even intervals; but rather, are moved at programmed intervals inputted by the user. For example, the user may input into the master controller 300 that the reaction vessels 160 are to be moved every minute for the first ten minutes and then every 5 minutes for time remaining in the study. Such a distribution yields more data points for the early time frame of the study.

The master controller 300 also permits the user to perform other operations, such as aborting the study and also locking and unlocking the robotic device 230. The exemplary master controller 300 has an abort button 425 for causing the study to be aborted upon the user invoking this function. At display 427, it is indicated whether the robotic device 230 is in a locked or unlocked position. The user may place the robotic device 230 in either position using any number of techniques including depressing a button (not shown) or manually manipulating a lever or the like on the robotic device 230 itself or the user may use the master controller 300 to change the position of the robotic device 230. For example, the user may depress a display button on the master controller 300 or otherwise indicate that the current position of the robotic device 230 is to be changed. Because the master controller 300 is operatively connected to the robotic device 230, the precise position of the robotic device 230 may easily be communicated therebetween. The operating system of the master controller 300 is programmed so that control signals including instructions for repositioning the robotic device 230 are sent from the master controller 300 to the device 210. The control signals are preferably generated by a central processor, e.g., a CPU, of the master controller 300 and are then delivered to the device 210 which in turn positions the robotic device 230 at a specific location using the coordinate processing system of the apparatus 100.

In one embodiment, the robotic device 230 is programmed to transfer reaction vessels 160 in a specific order from the hot reaction block 120. For example, the robotic device 230 will transfer the reaction vessels 160 by rows in that the robotic device 230 first transfers the reaction vessel 160 disposed in a first opening of a first row (e.g., upper left corner of block 120) and then next transfers the reaction vessel 160 in a second opening in the first row. The robotic device 230 is thus programmed so that it transfers reaction vessels 160 according to a programmed pattern in that each time the robotic device 230 receives a command signal to transfer one reaction vessel 160, it will move to the next coordinate location where a reaction vessel 160 is present.

A central display region 430 of the master controller 300 displays a temperature versus time graph generated by the master controller 300. This graph tracks the actual temperature of the hot block 120 as a function of time. This type of graph permits the user to easily see the progression of the study in terms of seeing the actual temperature of the hot block 120 as the study progresses. As shown in FIG. 7, the illustrated graph is generally linear in nature indicating that the temperature increased at a uniform rate over time as the study was conducted. This does not necessarily have to be the case and the temperature may increase in a nonuniform manner or the temperature may be constant throughout the kinetics study, e.g., isothermal study. In one exemplary embodiment, the master controller 300 includes a standard desktop computer (e.g., IBM 233 MHz, 32 MB RAM) which is used to perform the operations described herein.

The cold block 130 acts to quench the chemical reaction that is ongoing within the reaction vessels 160 that have each been heated to a predetermined temperature before being removed from the hot block 120. Thus, the cold block 130 is maintained at a low enough temperature that quenches the reaction that is occurring within the reaction vessels 160 transferred to the cold block 130. It will be appreciated that the cold block 130 may either be maintained at a constant temperature or the temperature may be varied as the study progresses. For example, it may be desirable in some studies for the temperature of the cold block 130 to progressively become colder as the study itself progresses. Because the cold block 130 and the temperature control device 190 and temperature monitoring device 200 thereof are in communication with the master controller 300, the controller 300 continuously monitors the temperature of the cold block 130 and makes sure that the cold block 130 is maintained at the proper temperature. The master controller 300 thus preferably transmits command signals to the temperature control device 190 based upon data received from the temperature monitoring device 200. It will be appreciated that the temperature control device 190 for the cold block 130 may be a self-contained unit that operates independently from the master controller 300. In this instance, the temperature control device 190 is programmed by the user before the study. For example, the temperature control device 190 may simply have an on-off switch along with a thermostat which the user sets to the predefined desired temperature. After being actuated, the device 190 will then simply cool the cold block 130 to this predefined desired temperature and maintain the cold block 130 at this temperature until the device is shut off.

While not shown in the FIGS., it will be understood that the user may enter as an input the desired temperature of the cold plate 130. In other words, there is preferably a cold block display screen (not shown) as part of the user interface 310 and the operating system thereof which permits the user to enter the temperature at which the cold block 130 is to be maintained. Furthermore, this screen preferably provides the user with the ability to program temperature and time profiles for the cold block 130 if so desired. In this manner, the temperature of the cold block 130 may be programmed to gradually decrease over the time of the study. As with the hot block 120, the cold block display screen may have a display window showing the temperature versus time of the cold block 130 as the study progresses and is finally completed. Because in many instances, the temperature of the cold block 130 is constant, this feature may not be needed.

The operation of the apparatus 100 will now be described with reference to FIGS. 2–10. After the user defines the parameters of a particular chemical reaction kinetics study, the user enters the appropriate input information into the master controller 300 using the user interface 310. For example and as previously-mentioned, the user will enter the number of samples which are to be used in the particular study. Each reaction vessel 160 represents a single data point and accordingly, by using more reaction vessels 160, more data points are generated and then fitted to a particular selected kinetics model. The use of more reaction vessels 160 yields more accurate results. The user also inputs both the temperature and time profiles using the techniques described hereinbefore. When each reaction vessel 160 includes a number of melting point capillary tubes, each vessel 160 represents a single data point for each of the samples disposed throughout the multiple tubes.

After identifying the experimental conditions using the user interface 310, the user loads the correct number of reaction vessels 160 into the preheated hot block 120. The hot block 120 may have a number of sensors with one sensor being associated with one opening 140 so that the master controller 300 receives a location signal from the sensor indicating that the particular opening 140 contains one reaction vessel 160. This information is then used by the operating system of the master controller 300 to both instruct the device 210 and also generate the simulated view of the hot block 120 as part of the display 390. If no sensors are used in the apparatus 100, the user simply loads the reaction vessels 160 according to a predefined arrangement. For example, the user loads the reaction vessels 160 by rows starting at one end of the row and once the first row is full, the user goes to the one end of the second row, etc.

Figure 4:
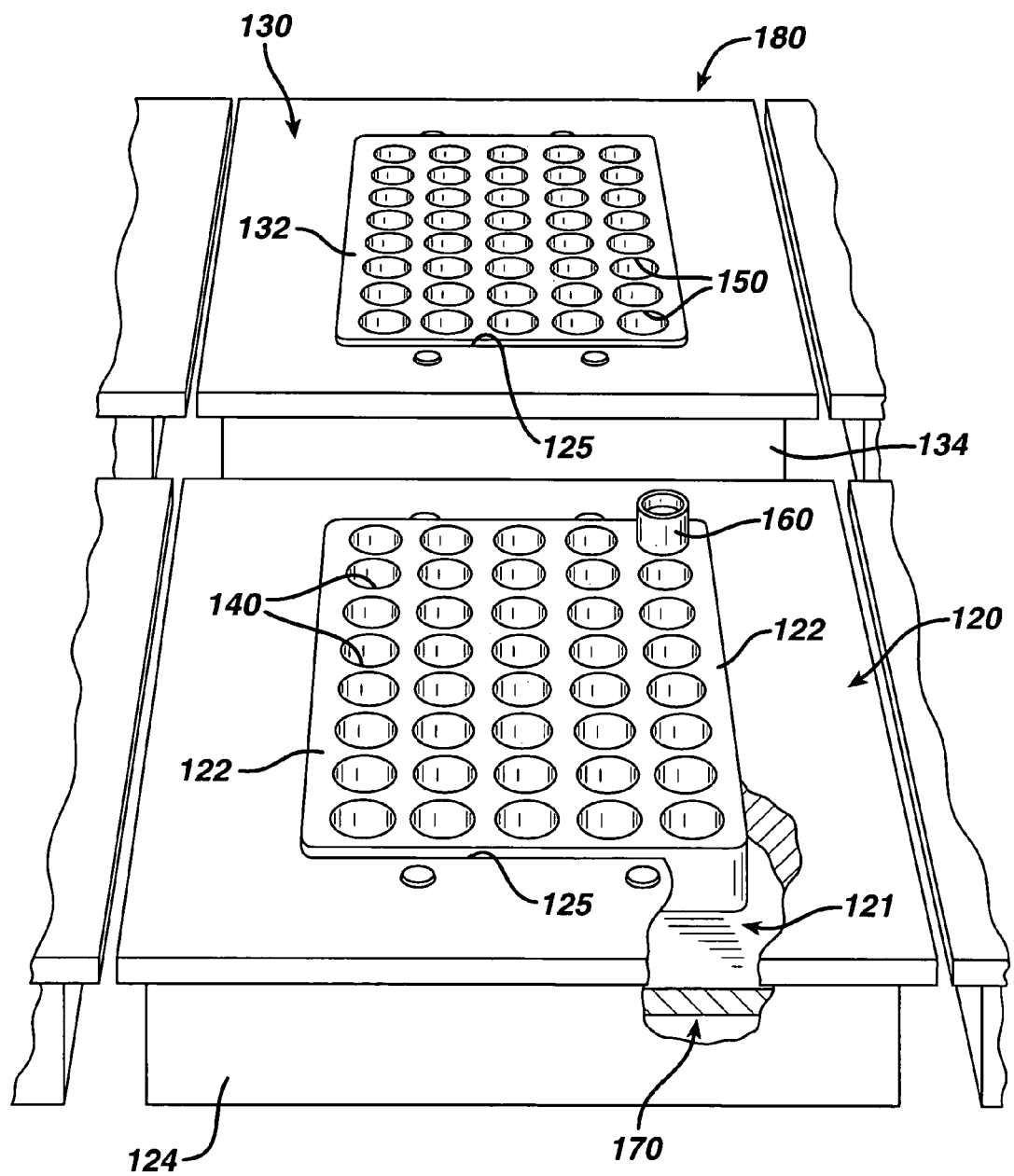
FIG. 4 is a top perspective view of hot and cold reaction blocks used in the apparatus of FIG. 3 with a portion broken thereaway.
Figure 5:
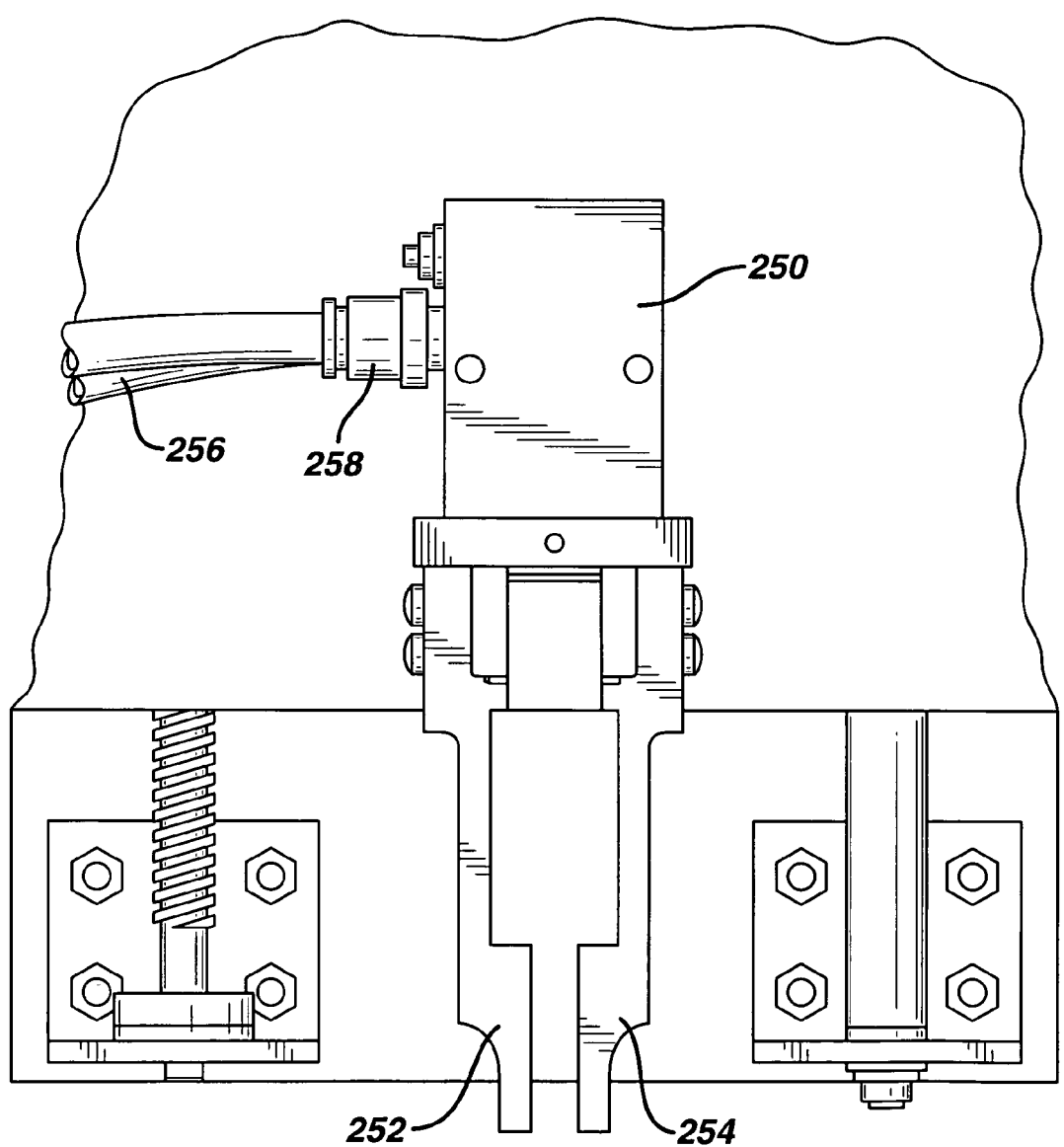
FIG. 5 is an enlarged side view of a gripping mechanism used in a robotic device of the apparatus of FIG. 3.

As best shown in FIGS. 3–5, each opening 140 or 150 of the respective reaction blocks has specific x, y, and z coordinates associated therewith and the programmable device 210 and the master controller 300 have conventional coordinate system processing. This permits the master controller 300 to receive location signals from the hot block 120 and then process the signals and create a coordinate map of the location of the reaction vessels 160 within the hot block 120. It will be appreciated that the cold block 130 contains similar sensors for indicating which of the openings 150 of the cold block 130 contain reaction vessels 160. This location information is used to generate the simulated view of the cold block 130 as part of the display 390 and this information is also used by the operating system to effectuate transfers of the reaction vessels 160 from the hot block 120 to the cold block 130. Accordingly, the operating system of the master controller 300 generates and stores a map showing the specific locations of all of the reaction vessels 160 based on the above-mentioned coordinate system. When no sensors are used, the map is generated based upon user inputs, e.g. number of reaction vessels 160, and it is necessary that the user place the vessels 160 according to the predefined arrangement.

In one embodiment, the robotic device 230 will transfer each reaction vessel 160 from one of the openings 140 of the hot block 120 to the opening 150 of the cold block 130 that has the same coordinates as the opening 140 from which the reaction vessel 160 was removed. For example, a reaction vessel 160 in the opening 140 having the coordinates $x_2$, $y_3$, $z_1$ will be transferred to the opening 150 having the coordinates $x_2$, $y_3$, $z_1$ which are associated with the cold block 130. It will be appreciated that the coordinates are not identical as there is additional addressing information. e.g., an address location for the hot and cold blocks 120, 130, which is included in the mapping and transfer operations; however, these operations are standard in the robotics field and suitable software is loaded and incorporated into the design of the robotic device 230. Thus for purpose of simplification, the present invention will be discussed as transferring the reaction vessel 160 from one mapped location in the hot block 120 (e.g., $x_2$, $y_3$, $z_1$) to a corresponding mapped location in the cold block 130 which has identical coordinates (e.g., $x_2$, $y_3$, $z_1$).

The study is then initiated and the master clock display 410 is actuated and begins logging the elapsed time of the study. In addition, the count-down clock 420 is also actuated at the same time and begins counting down and displaying the time until the next reaction vessel transfer is to be made. The master controller 300 communicates with the temperature control device 190 and preferably delivers command signals thereto for instructing the device 190 to either maintain or increase the temperature of the hot block 120 depending upon the temperature and time profiles inputted by the user and the corresponding temperature versus time graph generated therefrom.

It will be appreciated that the device 190 may have its own operating system so that it simply receives input signals from the master controller 300 and then determines a heating curve over time. In other words, after the user has inputted the temperature and time profiles using the user interface 310, the master controller 300 generates and delivers signals representative of this inputted information to the device 190. The device 190 then determines the precise temperature versus time graph which is to be followed during the study.

As the time for transferring the first reaction vessel 160 approaches, the master controller 300 communicates with the device 210 and more specifically, the robotic device 230 thereof and causes the main unit 240 to be positioned relative to the first reaction vessel 160 to be transferred. More specifically, the gripping mechanism 250 is moved above the first reaction vessel 160 such that the fingers 252 and 254 are disposed proximate to the first reaction vessel 160 which has a set of specific location coordinates, e.g., $x_2$, $y_3$, $z_1$. At the first transfer time, the master controller 300 instructs the robotic device 230 to begin the transfer operation by closing the fingers 252 and 254 about the first reaction vessel 160 resulting in the first reaction vessel 160 being securely gripped by the fingers 252, 254. As previously-mentioned, the gripping of the first reaction vessel 160 occurs when a pressure (e.g., 20 psi) is applied to the second line 258 and the first line 256 is vented causing the fingers 252, 254 to converge and grip the first reaction vessel 160 therebetween.

The robotic device 230 then lifts the first reaction vessel 160 from the respective opening 140 and after the first reaction vessel 160 clears the hot block 120, it is delivered to the corresponding opening 150 ($x_2$, $y_3$, $z_1$ coordinates) of the cold block 130. The first reaction vessel 160 is disposed within this opening 150 of the cold block 130 to thereby quench the chemical reaction and effectively store the first reaction vessel 160 at a sufficiently low temperature that ensures that the chemical reaction does not proceed within the first reaction vessel 160.

After the first reaction vessel 160 has been transferred, the graphical display of the blocks 120, 130 is updated in the display window 390. Importantly, the actual temperature of the hot block 120 is recorded at the first transfer time and the actual sampling time is also recorded. Because the temperature monitoring device 200 is preferably in continuous communication with the master controller 300, the actual temperature of the hot block 120 is received by the master controller 300 as a data stream and at the actual sampling time, the actual temperature of the hot block 120 is recorded and saved as a first data point. During the course of a study, the temperature controller 190 is updated every 0.1° C. change in the user defined temperature profile. If desired, a tab delimited file with time and temperature columns can be imported to the user interface 310. The tabs delimited text file logs actual temperature changes greater than 0.1° C. for either of the hot or cold blocks 120, 130. This file also captures the sampling time of each reaction vessel 160 and provides a convenient audit trail for the user. The components of the apparatus 100 may be configured in other ways so long as the actual temperature of the hot and cold blocks 120, 130 and the actual sampling time for a specific transfer are recorded and logged as a data point. Preferably and similarly, the actual temperature of the cold block 130 is also recorded and furthermore, the actual time that the first reaction vessel 160 is disposed within the opening 150 is also recorded.

Throughout the study, the other displays of the operating system of the user interface 310 are also continuously updated to permit the user to get real time conditions of the hot and cold blocks 120,130. For example, the thermometers 392, 394 are continuously updated based on information received from the temperature monitoring devices 200 and serve to display the current temperatures of the hot and cold blocks 120, 130, respectively.

After the first reaction vessel 160 is disposed within the corresponding opening 150 of the cold reaction block 130, the robotic device 230 is repositioned so that it may grasp and transfer a second reaction vessel 160 from the hot block 120 to the cold block 130. The master controller 300 instructs the robotic device 230 to the opening 140 associated with the second reaction vessel 160 and then at the second transfer time, the master controller 300 instructs the robotic device 230 to grasp the second reaction vessel 160 and transfer it to the corresponding opening 150 of the cold block 130. One will appreciate that the actual sampling time and the actual temperature of the hot block 120 for the transfer of the second reaction vessel 160 are recorded using the techniques described hereinbefore. The second reaction vessel 160 thus constitutes a second data point.

The collecting of data continues until all of the reaction vessels 160 are transferred from the hot block 120 to the cold block 130. When this is complete, the master controller 300 has received data associated with each specific transfer of one reaction vessel 160 from the hot block 120 to the cold block 130. More specifically, the master controller 300 receives at least the actual sampling time and actual temperature for each reaction vessel transfer. This information is stored and used to generate various displays for the user. For example, the master controller 300 is preferably designed so that user may generate any number of types of graphs for display and printout in addition to other computer-generated information.

As previously-mentioned, the robotic device 230 may later be used to automatically transfer the reaction vessels 160 from the cold block 130 to a testing instrument, such as an HPLC instrument (not shown). In this embodiment, the collection/transfer and testing operations may be automated using the single apparatus 100 of the present invention. For example, after the reaction vessels 160 have been stored in the cold block 130 for a set period of time, the user may instruct the robotic device 230, using the master controller 300, to transfer each of the reaction vessels 160 to the testing instrument. The master controller 300 preferably has the associated coordinates of the testing device stored therein and the master controller 300 will then pick-up each reaction vessel 160 from the cold block 130 and then deliver it to a predefined section of the testing instrument. After the sample in one specific reaction vessel 160 has been tested using the testing instrument, the reaction vessel 160 may either be transferred from the testing device to some other location, such as a sample location area, or the reaction vessel 160 may be returned to the cold block 130.

The apparatus 100 of the present invention offers many advantages. In particular, the apparatus 100 is more efficient in performing transferring and data logging operations than manual methods because after the apparatus 100 is setup by the user, these and other operations are carried out in a fully automated manner. The apparatus 100 provides the ability to run multiple reactions in parallel which allows higher throughput and cost savings. Another advantage of the present invention is the ability to input a temperature and sampling versus time program for each individual reaction block 120,130. This provides the user greater flexibility and also expands the types of applications which are available to the user. For example, the user has the ability to run non-isothermal and isothermal reactions in parallel. The apparatus 100 also provides flexibility for unforeseen developments in degradation kinetics. For example, temperature programs other than those listed in Table 1 may be easily programmed into the master controller 300 resulting in the user having another selection on a program menu from which to choose. For example, isothermal and other types of models may be programmed into the master controller 300 (operating system/user interface 310 thereof).

Because the apparatus 100 provides continuous data logging, a convenient audit trail is provided for the analysts. This feature also complies with standard operating procedures to ensure that the actual temperatures of a study follow user defined temperatures. Furthermore, because each reaction vessel 160 represents a single data point, there is no cross contamination between samples during the experiment and the use of HPLC autosampler vials (reaction vessels 160) is particularly well suited for these types of studies as the automated device 210 may be programmed to directly load these vials from the cold block 130 onto an HPLC instrument (not shown) for analysis thereof, as previously-mentioned.

The apparatus 100 of the present invention was used to conduct feasability studies in which a new developmental drug was used as a model compound for feasability studies. This drug was exceptionally stable under normal conditions and therefore the feasability studies were performed in solution at the extremes of pH (i.e., pH 1.0 and 11.7). The product distributions at each pH were similar across the temperature ranges that were studied; therefore, it was assumed the reaction mechanisms and degradation pathways were not a function of temperature.

Isothermal reactions at 85° C. were conducted (pH 1.0 and 11.7) and the results are shown in FIGS. 8A–9B and Table 2.

TABLE 2

Summary of Experimental Data for Kinetics Reactions of an Experimental Drug where $k_{obs}$ = apparent first-order rate constant

| Mode | Conditions | Temp. °C. | $k_{obs}$ $hr^{-1}$ | Error in $k_{obs}$ $hr^{-1}$ | RSD in $k_{obs}$ $hr^{-1}$ |
|---|---|---|---|---|---|
| Isothermal | pH 1.0, 85° C. | 85 | 0.030 | 0.001 | 3 |
| Nonisothermal | pH 1.0, 50–100° C. over 80 hrs. | 85 | 0.030 | 0.028 | 93 |
| Nonisothermal | pH 1.0, 50–150° C. over 20 hrs. | 85 | 0.049 | 0.040 | 80 |
| Isothermal | pH 11.7, 85° C. | 85 | 0.0094 | 0.0005 | 6 |
| Nonisothermal | pH 11.7, 50–100° C. over 160 hrs. | 85 | 0.0088 | 0.0050 | 56 |

Integration of the first-order rate equation (Equation 1) gives $Ln(C)=-kt+Ln(C_0)$. Therefore, the linear plots of Ln(C) versus time demonstrated first-order kinetics for the degradation at low and high pH.

Initial studies were conducted with linear heating programs. The experimental data (concentration of the drug versus time and temperature) were fit to the first-order kinetics model shown in Equation 3 with a software application known as SCIENTIST (Version 2; commercially available from MicroMath, Salt Lake City, Utah). This software application was used to solve the differential equation (Equation 3) directly.

The values for A and E (Equation 3) that resulted from the model fitting operation were then used to calculate rate constants (k) at specific temperatures with the Arrhenius equation (Equation 2). The calculated k's at 85° C. agreed fairly well with the corresponding values that were actually measured in the isothermal studies (Table 2). The errors in the k's calculated from the nonisothermal data can be significant in some instances, although this is also the case when using more traditional testing methods. There are a number of factors which can influence the amount of experimental error in resulting A, E, and k values. Based on further experiments, it was concluded that the following factors, in approximate order of importance, can influence the amount of experimental error in the resulting A, E, and k values: HPLC assay, vial leakage and condensation problems, the chosen temperature program (nonlinear is better), number of data points collected (more is better), number of half lives followed, initial parameter guesses (A and E) for model fitting, and non-uniform sample storage prior to HPLC analysis.

The apparatus 100 described here minimized errors due to sample storage, temperature control and precise sampling intervals. Uniform sampling intervals are desired for nonisothermal reactions because of the temperature dependence on time. Because the temperature controller and sampling device are integrated into one apparatus, precise sampling is not a problem. Temperature control of the hot block 120 has been shown to be accurate for a typical nonisothermal run, providing a perfect correlation ($r^2=1.00$) between desired and actual temperatures. The invention was also capable of storing vials at 4° C. and thus provided uniform sample storage prior to HPLC analysis. Therefore, the apparatus was essential to minimize these errors in the study.

One principle source of experimental error in the final calculated k's was determined to be the HPLC assay (Table 3) as shown by simulated data.

TABLE 3

Selected Simulations (A = 2.54 × $10^{10}h^{-1}$, E = 20.42 Kcal/mole; equivalent to k = 0.0088 $h^{-1}$ at 85° C.). Simulated data were fit with initial conditions of A = 1.4 × $10^{10}h^{-1}$ and E = 20 Kcal/mole. $k_{obs}$ = apparent first-order rate constant

| Error | Temp. Program | A, $h^{-1}$ | Error in A, $h^{-1}$ | Eact (Kcal/mole) | Error in Eact (Kcal/mole) | ° C. | $k_{obs}$, $h^{-1}$ | Error in $k_{obs}$, $h^{-1}$ | $k_{obs}$ RDS, calcd |
|---|---|---|---|---|---|---|---|---|---|
| 0% | Linear | 1.40 × $10^{10}$ | 2.53 × $10^{9}$ | 20.00 | 0.13 | 85 | 0.0087 | 0.0021 | 24 |
| 0.5% | Linear | 1.40 × $10^{10}$ | 3.40 × $10^{9}$ | 20.00 | 0.17 | 85 | 0.0087 | 0.0028 | 32 |
| 1% | Linear | 1.74 × $10^{10}$ | 7.32 × $10^{9}$ | 20.15 | 0.30 | 85 | 0.0088 | 0.0048 | 54 |
| 1% | UDUD | 2.25 × $10^{10}$ | 3.86 × $10^{9}$ | 20.34 | 0.12 | 85 | 0.0088 | 0.0021 | 23 |

The simulated data was obtained by using SCIENTIST to generate a data set (molarity versus time/temperature data) with equation 3. A known amount of random error was introduced into the molarity values (with EXCEL™). This data was then fit to Equation 3 with SCIENTIST. In one trial, 1% error was introduced into a data set that was created to mimic the actual data set for the pH 11.7 nonisothermal experiment (Table 2). SCIENTIST predicted a k value with an RSD of 54% which compared well with the 56% RSD that was obtained for the real data set. Thus the nominal 1% error normally expected with HPLC determinations is sufficient to account for the majority of our observed experimental errors. If the error in the HPLC assay could be reduced to 0.5%, then the corresponding error in k would be 32% (Table 2).

Figure 10A:
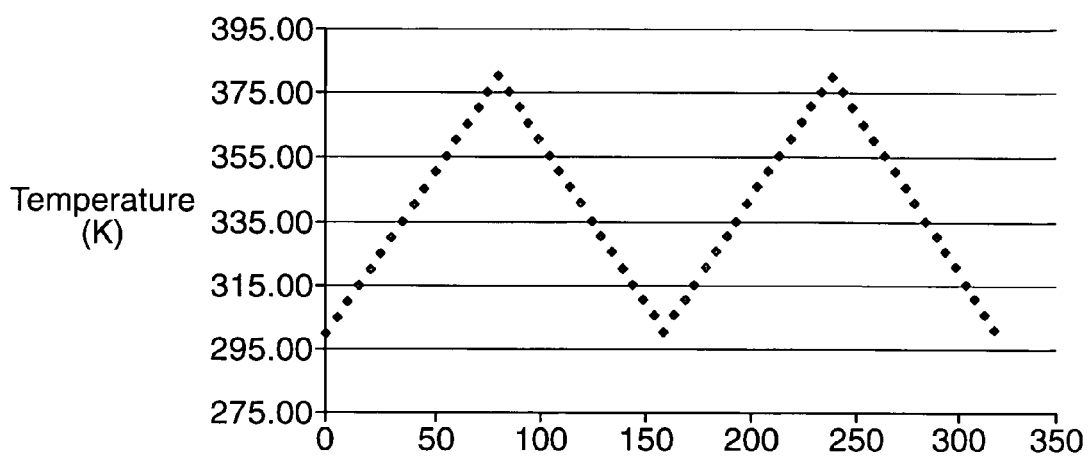
FIG. 10A is a graph obtained from an exemplary double heating/cooling program ("UDUD" for up/down/up/down program)
Figure 10B:
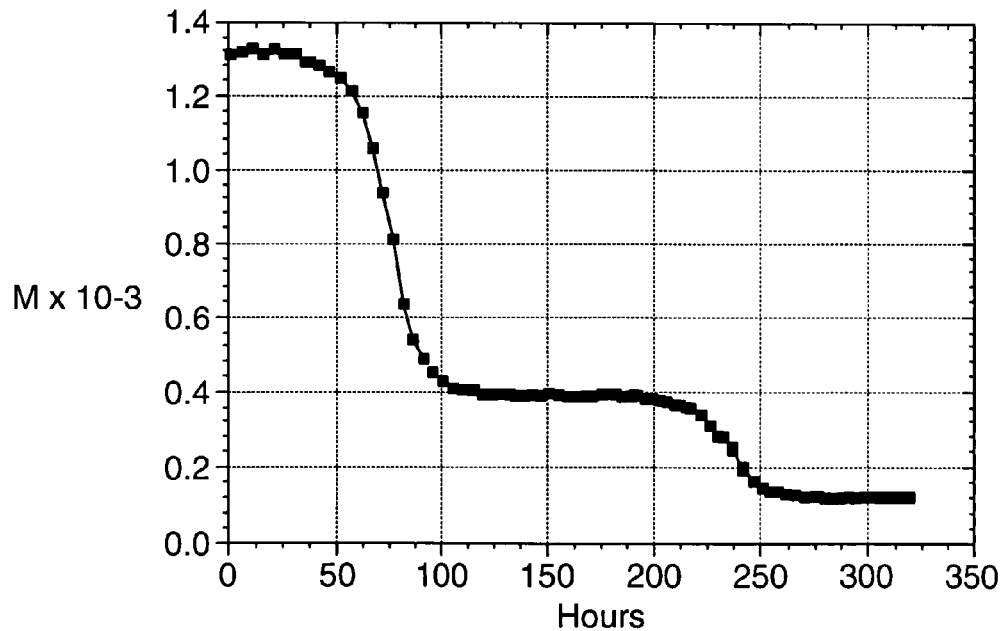
FIG. 10B is a graph of the corresponding simulated nonisothermal data being shown obtained running the program of FIG. 10A.

Since in practice the HPLC errors cannot be reduced below 0.5–1%, other alternatives for decreasing the experimental errors were considered in predicted rate constants. The use of nonlinear temperature programs is an important approach. Simulations were performed as described above for numerous nonlinear heating and heating/cooling programs. One double heating/cooling program ("UDUD" or up/down/up/down program) is illustrated in FIG. 10A along with the resulting simulated data set shown in FIG. 10B. The UDUD program produced a molarity versus time curve that had far more curvature than the corresponding curves from linear temperature programs (compare FIGS. 8A–B, 9A–B, and 10A–B). This increased curvature facilitated the model fitting operation in SCIENTIST. Initial guesses for A and E did not have to be as close to the actual values as was necessary with data obtained with linear temperature programs. Furthermore, the UDUD temperature program resulted in reduced errors in the predicted rate constants from simulated data with 1% random error (Table 3). The UDUD program has not yet evaluated in actual experiments but the apparatus is capable of producing this temperature profile.

Isothermal and (optimized) nonisothermal experiments should give similar experimental errors. Isothermal studies at multiple temperatures preferably include 12–20 points/reaction×4–6 reactions=48–120 points. Nonisothermal studies preferably include (40 points/nonisothermal reaction×1 reaction)+(12–20 points for isothermal reaction×0–1 reactions (model confirmation and product distribution versus time)=40–60 points. Thus fewer reactions and fewer HPLC analyses are required for nonisothermal studies. The reduction in the number of reactions is an enormous advantage for the nonisothermal approach since our robotics capacity is limited. Nonisothermal reactions require less knowledge of approximate rates before the laboratory experiments are conducted. Thus with the nonisothermal approach fewer experiments will have to be discarded because of reaction rates being too slow or too fast for the rate of sample collection.

Isothermal reactions at lower temperatures could take months. However, first-order plots are linear and conceivably less than one half life could suffice. Corresponding nonisothermal studies would also be lengthy (2–3 half lives are desired) but the total time will probably be less than time for isothermal studies. In summary, nonisothermal studies will require fewer reactions (less demand for limited robotics capacity), less total time, fewer HPLC samples, and less documentation requirements. It will be appreciated that the foregoing experimental studies are merely exemplary and do not limit the present invention.

Accordingly, the apparatus 100 of the present invention is capable of conducting kinetics studies with user-defined temperature profiles and sampling periods. Because temperature profiles and sampling periods can be programmed independently on each reaction block 110, parallel reactions may be run during the study. This results is higher throughput and cost savings.

While the invention has been particularly shown and described with reference to preferred embodiments thereof, it will be understood by those skilled in the art that various changes in form and details may be made therein without departing from the spirit and scope of the invention.

What is claimed is:

1. An automated apparatus for performing reaction kinetics studies, the apparatus comprising:
    a plurality of reaction blocks including at least one hot reaction block that heats one or more reaction vessels and at least one cold reaction block that cools the one or more reaction vessels after heating thereof;
    a robotic device that transfers one reaction vessel from one hot reaction block to one cold reaction block; and a controller having a user interface for inputting a predetermined temperature profile and a predetermined sampling interval, the controller being in communication with the plurality of reaction blocks and the robotic device so as to instruct the robotic device to transfer one reaction vessel from one hot reaction block to one cold reaction block at a predefined transfer time within the predetermined sampling interval, the predetermined temperature profile representing the temperature of at least one of the hot reaction blocks over a time period of the study;

wherein the controller is configured so that both isothermal and nonisothermal temperature reactions are performed in the same apparatus.

2. The apparatus of claim 1, wherein each of the hot and cold reaction blocks has a plurality of openings formed therein, one opening receiving one reaction vessel.

3. The apparatus of claim 1, further including:
a heating device associated with each of the hot reaction blocks that controls heating thereof; and
a cooling device associated with each of the cold reaction blocks that controls cooling thereof, wherein each of the heating and cooling devices is in communication with the controller.

4. The apparatus of claim 3, wherein the heating device heats the hot reaction blocks according to the predetermined temperature profile.

5. The apparatus of claim 1, wherein the predetermined temperature profile includes an initial temperature and a final temperature, the predetermined temperature profile being defined by the initial temperature and the final temperature.

6. The apparatus of claim 1, wherein the predetermined sampling interval includes a study start time and a study stop time with the sampling interval being the time period beginning with the start time and ending with the stop time of the study.

7. The apparatus of claim 1, wherein the robotic device moves in three dimensions relative to the plurality of reaction blocks so as to permit the robotic device to grasp and transfer the plurality of reaction vessels.

8. The apparatus of claim 1, wherein the robotic device has a gripping mechanism that grips and transfers one reaction vessel from the hot reaction block to the cold reaction block at the predefined transfer time.

9. The apparatus of claim 8, wherein the gripping mechanism is operated by toggling a predetermined pressure between first and second lines such that the gripping mechanism closes to securely engage one reaction vessel for transfer from the hot reaction block to the cold reaction block when a pressure is applied to the first line with the second line being vented, the gripping mechanism opening to release the one reaction vessel when the pressure is applied to the second line with the first line being vented.

10. The apparatus of claim 8, wherein the gripping mechanism includes a first finger and a second opposing finger with a space therebetween, one reaction vessel being disposed within the space and held between the first and second fingers during the transfer of the one reaction vessel from the hot reaction block to the cold reaction block.

11. The apparatus of claim 1, wherein the controller includes a master clock and a count-down clock, the master clock displaying the sampling interval for the study and the count-down clock counting down the time before the next transfer of one of the reaction vessels.

12. The apparatus of claim 1, wherein the master controller includes a user interface configured to input the predetermined temperature profile and the predetermined sampling interval.

13. The apparatus of claim 1, further including:
a temperature control device operatively connected to one or more of the hot and cold reaction blocks that controls a temperature of each of the hot and cold reaction blocks, the temperature control device being in communication with the controller, and
a temperature monitoring device that monitors the temperature within at least one of the hot and cold blocks, the temperature monitoring device being in communication with the controller so as to provide the controller with temperature data representing the temperature of one or more of the hot and cold blocks.

14. The apparatus of claim 13, wherein the temperature control device comprises one of a single loop, dual loop, and multi-loop temperature controller.

15. The apparatus of claim 13, wherein the temperature monitoring device is a resistance temperature detector.

16. The apparatus of claim 1, wherein data associated with a chemical reaction occurring in each reaction vessel is collected and logged as a single data point that is displayed on a corresponding graph.

17. An automated apparatus for performing reaction kinetics studies, the apparatus comprising:
a plurality of reaction blocks including at least one hot reaction block that heats one or more reaction vessels and at least one cold reaction block that cools the one or more reaction vessels after heating thereof;
a robotic device that transfers one reaction vessel from one hot reaction block to one cold reaction block; and
a controller having a user interface configured to input a predetermined temperature profile and a predetermined sampling interval, the controller being in communication with the plurality of reaction blocks and the robotic device so as to instruct the robotic device to transfer one reaction vessel from one hot reaction block to one cold reaction block at a predefined transfer time within the predetermined sampling interval, the predetermined temperature profile representing the temperature of at least one of the hot reaction blocks over a time period of the study;
wherein the predetermined temperature profile is an isothermal temperature profile.

18. An automated apparatus for performing reaction kinetics studies, the apparatus comprising:
a plurality of reaction blocks including at least one hot reaction block that heats one or more reaction vessels and at least one cold reaction block that cools the one or more reaction vessels after heating thereof;
a robotic device that transfers one reaction vessel from one hot reaction block to one cold reaction block;
a controller having a user interface configured to input at least (1) a number of reaction vessels for the study, (2) a first predetermined temperature profile and a second predetermined temperature profile, (3) a predetermined study time period beginning with a start time and ending with a stop time, and (4) a selected kinetics model, wherein the controller is in communication with the hot and cold reaction blocks and the robotic device, the controller including an operating system which instructs the robotic device to transfer the plurality of reaction vessels from one hot reaction block to one cold reaction block at predefined transfer times and wherein at least one of the hot reaction blocks is heated according to the first predetermined temperature profile over the study time period, the controller collecting and storing kinetics data for each reaction vessel transfer, the kinetics data at least including a temperature of the hot reaction block at each transfer time and a sampling time when each reaction vessel transfer from the hot reaction block to the cold reaction block occurred; and wherein the kinetics data is fitted to the selected kinetics model inputted by the user to generate a representative temperature vs. time graph, wherein the first predetermined temperature profile is a nonisothermal temperature profile and the second predetermined temperature profile comprises an isothermal temperature profile.

19. An automated apparatus for performing reaction kinetics studies, the apparatus comprising:

a plurality of reaction blocks including at least one hot reaction block that heats one or more reaction vessels and at least one cold reaction block that cools the one or more reaction vessels after heating thereof;

a robotic device that transfers one reaction vessel from one hot reaction block to one cold reaction block;

a controller having a user interface configured to input at least (1) a number of reaction vessels for the study, (2) a first predetermined temperature profile and a second predetermined profile, (3) a predetermined study time period beginning with a start time and ending with a stop time, wherein the controller is in communication with the hot and cold reaction blocks and the robotic device, the controller including an operating system which instructs the robotic device to transfer the plurality of reaction vessels from one hot reaction block to one cold reaction block at predefined transfer times and wherein at least one of the hot reaction blocks is heated according to the first predetermined temperature profile over the study time period, the controller collecting and storing kinetics data for each reaction vessel transfer, the kinetics data at least including a temperature of the hot reaction block at each transfer time and a sampling time when each reaction vessel transfer from the hot reaction block to the cold reaction block occurred; and wherein the user interface has a first display screen having a first display window where a temperature vs. time graph for the study is displayed and a plurality of a user input display windows which display user inputted information including the predetermined temperature profile and the predetermined study time period and the number of reaction vessels, wherein the first predetermined temperature profile is a nonisothermal temperature profile and the second temperature profile comprises an isothermal temperature profile.

20. The apparatus of claim 19, wherein the hot reaction block has a number of openings formed therein that receives a number of reaction vessels, the hot reaction blocks being connected to one or more heating devices with one or more temperature control devices being associated with the one or more heating devices that sets the temperature of one or more hot reaction blocks and wherein each cold reaction block has a number of openings formed therein for receiving a number of reaction vessels, the cold reaction blocks being connected to one or more cooling devices with one or more temperature control devices being associated with the one or more cooling devices.

21. The apparatus of claim 19, wherein the user interface includes a model fit window where a selected model fit program is displayed and the kinetics data is fitted to the desired kinetics model fit program to generate the temperature vs. time graph.

22. The apparatus of claim 19, wherein the controller includes a master control display screen having simulated hot and cold reaction block displays which indicate locations of the reaction vessels within each of the hot and cold reaction blocks.

23. The apparatus of claim 22, wherein the master control display screen has a thermometer display associated with each of the hot and cold reaction blocks, each thermometer display having a graphic thermometer display indicating a temperature of the associated one of the hot and cold reaction blocks and a second display window that numerically indicates the temperature of the associated one of the hot and cold reaction blocks.

24. The apparatus of claim 19, wherein the robotic device includes a gripping mechanism that grips and transfers one reaction vessel from the hot reaction block to the cold reaction block at one of the predefined transfer times.

25. The apparatus of claim 24, wherein the gripping mechanism includes a first finger and a second opposing finger with a space therebetween, one reaction vessel being disposed within the space and held between the first and second fingers during the transfer of the one reaction vessel from the hot reaction block to the cold reaction block.

26. The apparatus of claim 24, wherein the controller includes a master clock and a count-down clock, the master clock displaying a remaining time left in the study and the count-down clock displaying a remaining time before the next transfer of one of the reaction vessels.

27. A method of performing reaction kinetics studies and collecting data using an automated apparatus, the method comprising:

providing the automated apparatus, the apparatus including:

a plurality of reaction blocks including at least one hot reaction block that heats one or more reaction vessels and at least one cold reaction block that cools the one or more reaction vessels after heating thereof;

a robotic device that transfers one reaction vessel from one hot reaction block to one cold reaction block; and a controller having a user interface and being in communication with the robotic device;

entering a first input using the user interface, the first input corresponding to a number of reaction vessels used in the study;

entering a second input using the user interface, the second input corresponding to an isothermal temperature profile which represents the temperature of at least one of the hot reaction blocks over a time period of the study;

entering a third input using the user interface, the third input corresponding to a nonisothermal temperature profile which represents the temperature of at least one of the hot reaction blocks over a time period of the study;

entering a fourth input using the user interface, the fourth input corresponding to the time period of the study beginning with a start time and ending with a stop time;

transferring the reaction vessels at predefined transfer times, the predefined transfer times being calculated using the first and fourth inputs, each reaction vessel being transferred from one hot reaction block to one cold reaction block by the robotic device which receives command signals from the controller;

collecting kinetics data including at least a temperature of the hot reaction block at each transfer time and a sampling time indicating when each reaction vessel transfer occurred; and fitting the kinetics data to an inputted kinetics model.

28. A method of performing reaction kinetics studies and collecting data using an automated apparatus, the method comprising:

providing the automated apparatus, the apparatus including:
a plurality of reaction blocks including at least one hot reaction block that heats one or more reaction vessels and at least one cold reaction block that cools the one or more reaction vessels after heating thereof;
a robotic device that transfers one reaction vessel from one hot reaction block to one cold reaction block;
a controller having a user interface and being in communication with the robotic device;
entering a first input using the user interface, the first input corresponding to a number of reaction vessels used in the study;
entering a second input using the user interface, the second input corresponding to a predetermined isothermal temperature profile which represents the temperature of at least one of the hot reaction blocks over a time period of the study;
entering a third input using the user interface, the third input corresponding to a predetermined non-isothermal temperature profile which represents the temperature of another of the hot reaction blocks over a time period of the study;
entering a fourth input using the user interface, the fourth input corresponding to the time period of the study beginning with a start time and ending with a stop time;
transferring the reaction vessels at predefined transfer times, the predefined transfer times being calculated using the first and fourth inputs, each reaction vessel being transferred from one hot reaction block to one cold reaction block by the robotic device which receives command signals from the controller; and
collecting kinetics data including at least a temperature of the hot reaction block at each transfer time and a sampling time indicating when each reaction vessel transfer occurred,
entering a fifth input using the user interface, the fifth input representing a model fit program to which the kinetics data is fitted to generate a representative temperature vs. time graph.

29. The method of claim 28, wherein transferring the reaction vessels comprises:
sending a signal from the controller to the robotic device causing a gripping mechanism of the robotic device to be positioned at a predefined coordinate location relative to one of the hot reaction blocks where the gripping mechanism is instructed to securely grasp one of the reaction vessels, the one reaction vessel then being delivered to one of the cold reaction blocks for storage thereat.

30. The method of claim 28, wherein the gripping mechanism includes a first finger and a second finger with a space therebetween, one reaction vessel being disposed within the space and held between the first and second fingers during the transfer, the gripping mechanism being operated by:
toggling a predetermined pressure between first and second lines, the gripping mechanism closing about the one reaction vessel when the pressure is applied to the first line and the second line is vented, the gripping mechanism being opened to release the one reaction vessel by applying the pressure to the second line with the first line being vented.

31. The method of claim 28, wherein the at least one hot reaction block is heated by a heating device, the heating device having a temperature control device and a temperature monitoring device associated therewith, the temperature control device maintaining the temperature of the at least one hot reaction block according to the first input.

32. The method of claim 31, further including:
entering a sixth input using the user interface, the sixth input being a value for the number of reaction vessels to be transferred at each predefined transfer time; and
transferring the reaction vessels according to the sixth input.

33. The method of claim 28, wherein the fifth input is selected from the group consisting of a logarithmic fit, a reciprocal fit, a linear fit, an exponential fit, and a power function of time fit.

34. A method of performing reaction kinetics studies and collecting data using an automated apparatus, the method comprising:

providing the automated apparatus, the apparatus including:
a plurality of reaction blocks including at least one hot reaction block that heats one or more reaction vessels and at least one cold reaction block that cools the one or more reaction vessels after heating thereof;
a robotic device that transfers one reaction vessel from one hot reaction block to one cold reaction block;
a controller having a user interface and being in communication with the robotic device;
entering a first input using the user interface, the first input corresponding to a number of reaction vessels used in the study;
entering a second input using the user interface, the second input corresponding to a predetermined temperature profile which represents the temperature of at least one of the hot reaction blocks over a time period of the study;
entering a third input using the user interface, the third input corresponding to the time period of the study beginning with a start time and ending with a stop time;
transferring the reaction vessels at predefined transfer times, the predefined transfer times being calculated using the first and third inputs, each reaction vessel being transferred from one hot reaction block to one cold reaction block by the robotic device which receives command signals from the controller; and
collecting kinetics data including at least a temperature of the hot reaction block at each transfer time and a sampling time indicating when each reaction vessel transfer occurred,
performing multiple kinetics studies in parallel by having at least one hot reaction block and at least one cold reaction block associated with a first run and at least one hot reaction block and at least one cold reaction block associated with a second run, wherein at least one of the first, second and third inputs is different between the first and second runs, wherein the first run is an isothermal run and the second run is a non-isothermal run.

* * * * *